US012070241B2

(12) United States Patent
Franco et al.

(10) Patent No.: US 12,070,241 B2
(45) Date of Patent: Aug. 27, 2024

(54) SYSTEMS AND METHODS FOR HAIR TRANSPLANT

(71) Applicant: THE GENERAL HOSPITAL CORPORATION, Boston, MA (US)

(72) Inventors: Walfre Franco, Westborough, MA (US); Esmeralda Ibarra-Silva, Boston, MA (US); William A. Farinelli, Boston, MA (US); Joshua Tam, Boston, MA (US); R. Rox Anderson, Boston, MA (US); Lynn Drake, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 379 days.

(21) Appl. No.: 16/629,657

(22) PCT Filed: Jul. 16, 2018

(86) PCT No.: PCT/US2018/042303
§ 371 (c)(1),
(2) Date: Jan. 9, 2020

(87) PCT Pub. No.: WO2019/014677
PCT Pub. Date: Jan. 17, 2019

(65) Prior Publication Data
US 2021/0145476 A1  May 20, 2021

Related U.S. Application Data

(60) Provisional application No. 62/587,758, filed on Nov. 17, 2017, provisional application No. 62/532,892, filed on Jul. 14, 2017.

(51) Int. Cl.
*A61B 17/3205* (2006.01)
*A61B 17/00* (2006.01)
(Continued)

(52) U.S. Cl.
CPC ........... *A61B 17/32053* (2013.01); *A61B 2017/00367* (2013.01); *A61B 2017/00752* (2013.01);
(Continued)

(58) Field of Classification Search
CPC ......... A61B 17/3468; A61B 17/32053; A61B 2017/00367; A61B 2017/00752;
(Continued)

(56) References Cited

U.S. PATENT DOCUMENTS 3,007,471 A   11/1961   McClure
4,476,864 A   10/1984   Tezel
(Continued)

FOREIGN PATENT DOCUMENTS

CN   101584593 A   11/2009
CN   102665579 A   9/2012
(Continued)

OTHER PUBLICATIONS

International Searching Authority, International Search Report and Written Opinion for application PCT/US2018/042303, mailed on Sep. 27, 2018.

*Primary Examiner* — Sarah A Long
(74) *Attorney, Agent, or Firm* — Quarles & Brady LLP

(57) ABSTRACT

Systems and methods are provided for performing a hair transplant using a hair transplant device. The hair transplant device comprises a coring needle, a splitting needle, a housing, and a user interface. The coring needle forms a coring lumen configured to extract a hair follicle from a donor site. The splitting needle is configured to create an opening in a recipient site. The housing at least partially surrounds one of the coring needle and the splitting needle. The user interface extends from the housing and is movable relative to the coring needle to push the hair follicle from the
(Continued)

coring lumen into the opening in the recipient site formed by the splitting needle.

25 Claims, 21 Drawing Sheets

(51) Int. Cl.
 *A61B 17/32* (2006.01)
 *A61B 17/34* (2006.01)
 *A61B 90/00* (2016.01)
(52) U.S. Cl.
 CPC ........... *A61B 2017/00969* (2013.01); *A61B 2017/320064* (2013.01); *A61B 2017/3454* (2013.01); *A61B 2090/034* (2016.02)
(58) Field of Classification Search
 CPC ......... A61B 2017/00969; A61B 2017/320064; A61B 2017/3454; A61B 2090/34
 See application file for complete search history.

(56) References Cited

U.S. PATENT DOCUMENTS

| | | |
|---|---|---|
| 4,693,257 A | 9/1987 | Markham |
| 5,584,581 A | 12/1996 | Keller |
| 5,611,811 A | 3/1997 | Goldberg |
| 5,951,572 A | 9/1999 | Markman |
| 6,419,641 B1 | 7/2002 | Mark |
| 6,461,369 B1 | 10/2002 | Kim |
| 6,585,746 B2 | 7/2003 | Gildenberg |
| 7,261,721 B2 | 8/2007 | Feller |
| 7,452,367 B2 | 11/2008 | Rassman |
| 8,152,827 B2 | 4/2012 | Oostman, Jr. |
| 2003/0083621 A1 | 5/2003 | Shaw |
| 2003/0097144 A1 | 5/2003 | Lee |
| 2004/0220589 A1* | 11/2004 | Feller ............... A61B 17/32053 606/133 |
| 2005/0054948 A1 | 3/2005 | Goldenberg |
| 2005/0096687 A1* | 5/2005 | Rassman ............ A61B 17/3468 606/187 |
| 2006/0216781 A1 | 9/2006 | Gebing |
| 2007/0078473 A1* | 4/2007 | Bodduluri ............. A61B 34/70 606/167 |
| 2007/0106307 A1 | 5/2007 | Bodduluri |
| 2008/0051806 A1 | 2/2008 | Cole |
| 2008/0234697 A1 | 9/2008 | Dubois |
| 2010/0125287 A1* | 5/2010 | Cole ............... A61B 17/32053 606/133 |
| 2013/0226214 A1 | 8/2013 | Okuda |
| 2014/0296612 A1 | 10/2014 | Schwartz |
| 2014/0358028 A1* | 12/2014 | Vetter ................ A61B 10/0266 600/567 |
| 2015/0289624 A1 | 10/2015 | Abdullah |
| 2016/0317170 A1 | 11/2016 | Knowlton |
| 2016/0345999 A1 | 12/2016 | Oostman, Jr. |
| 2017/0020565 A1 | 1/2017 | Bae |
| 2017/0020566 A1 | 1/2017 | Bae |
| 2017/0143434 A1 | 5/2017 | Jung |

FOREIGN PATENT DOCUMENTS

| | | |
|---|---|---|
| EP | 0366336 A1 | 5/1990 |
| EP | 2939617 B1 | 11/2015 |
| JP | 2012196486 A | 10/2012 |
| WO | 2000064379 A1 | 11/2000 |
| WO | 2005077285 A1 | 8/2005 |
| WO | 2011140497 A2 | 11/2011 |

* cited by examiner

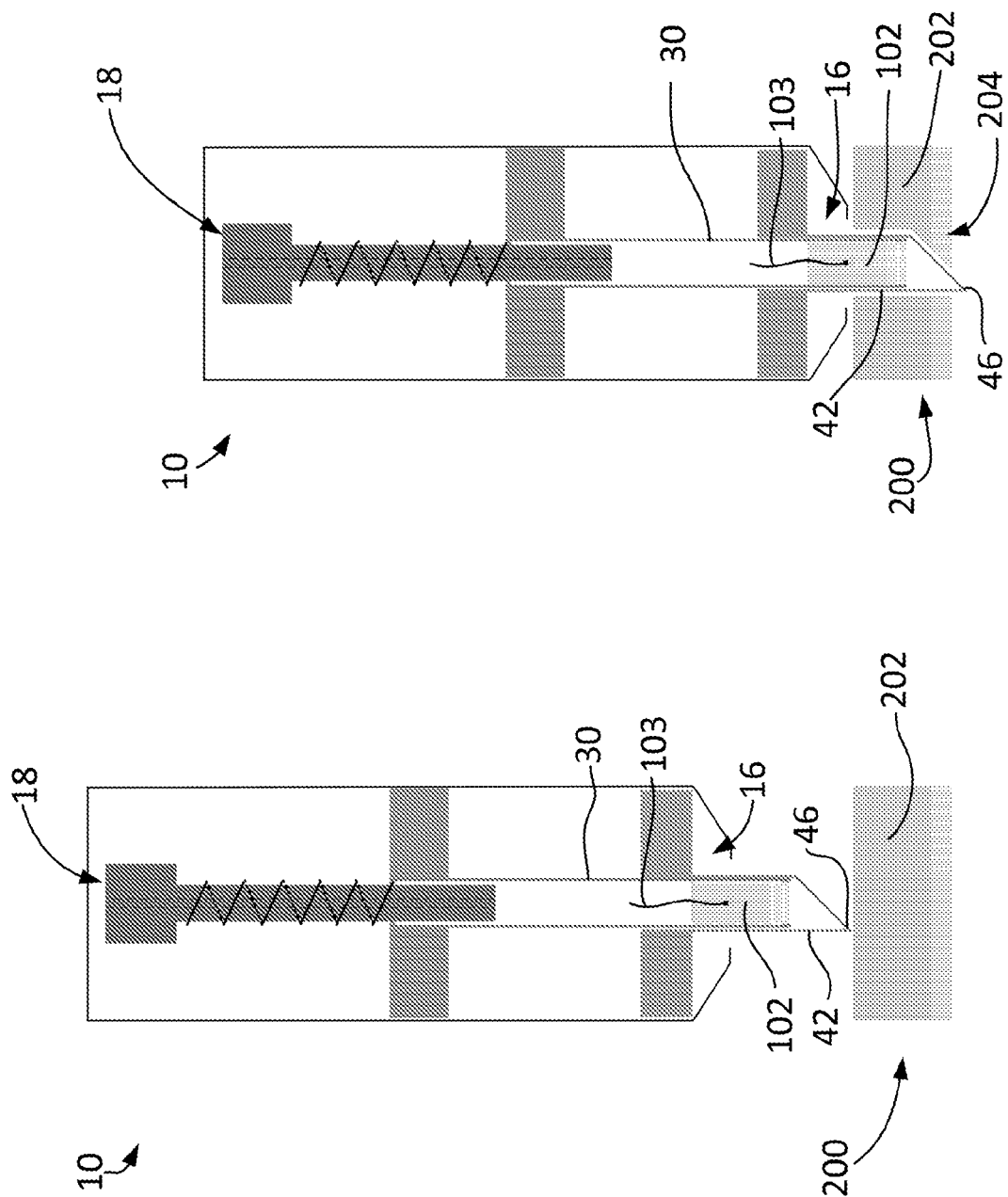

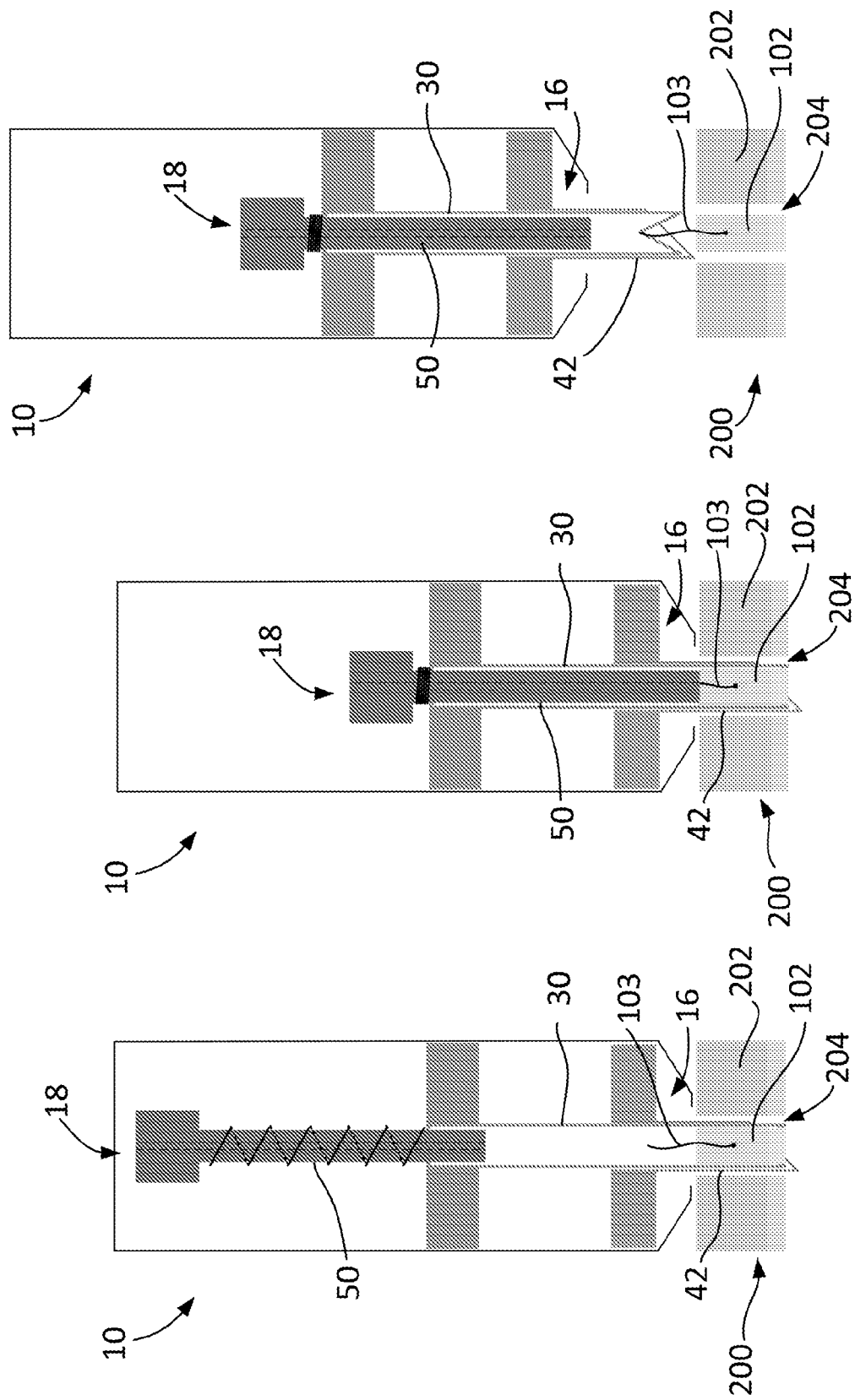

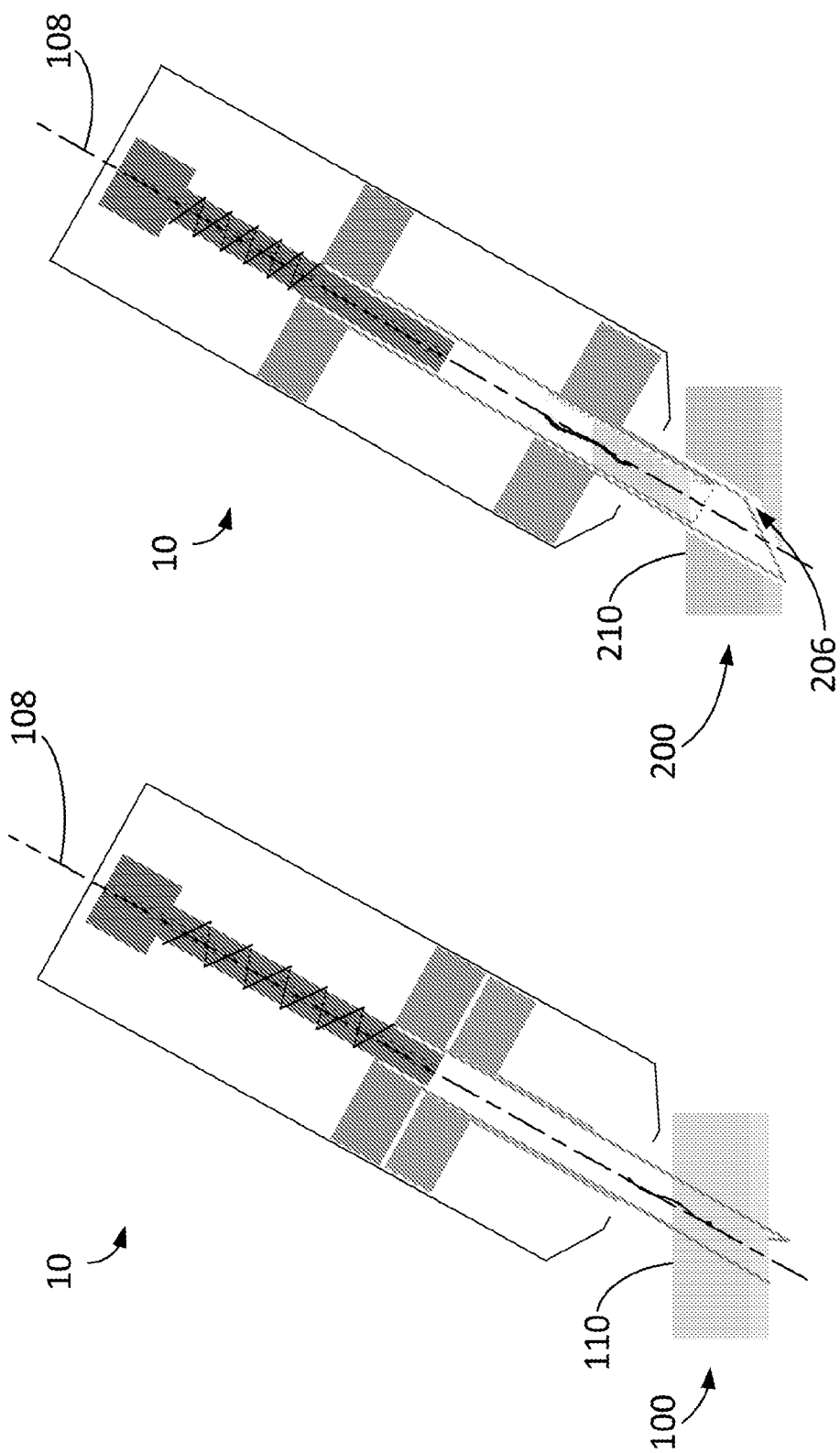

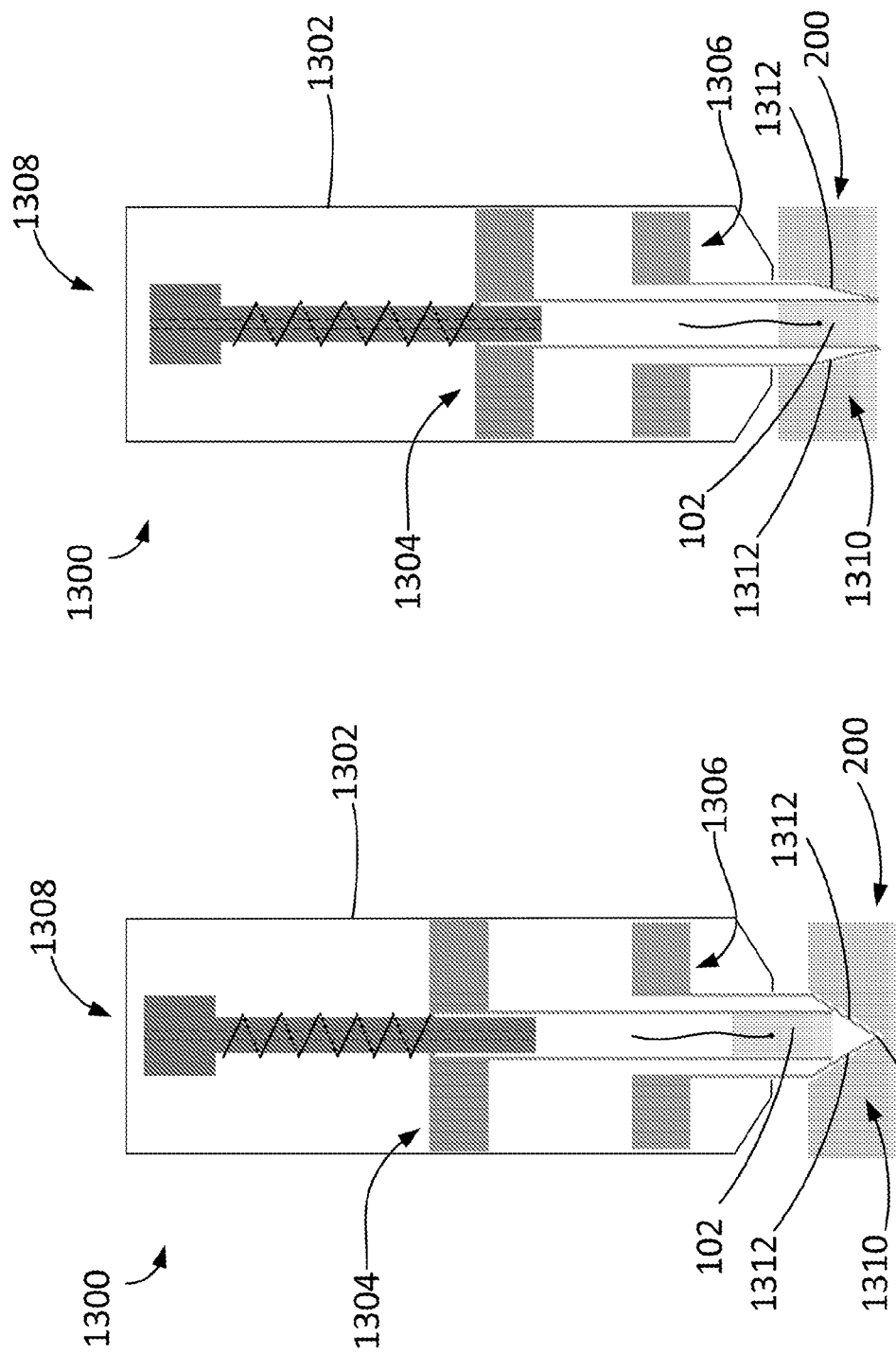

SYSTEMS AND METHODS FOR HAIR
TRANSPLANT

CROSS-REFERENCE TO RELATED
APPLICATIONS

This application is a U.S. National Phase of PCT Application No. PCT/US2018/042303 filed on Jul. 16, 2018, which is based on, claims the benefit of, and incorporates herein by reference in their entirety U.S. Provisional Patent Application Ser. No. 62/532,892, filed on Jul. 14, 2017, and U.S. Provisional Patent Application Ser. No. 62/587,758, filed on Nov. 17, 2017.

STATEMENT REGARDING FEDERALLY
SPONSORED RESEARCH

This invention was made with government support under AI083214 awarded by the National Institutes of Health, and 1755698 awarded by the National Science Foundation. The government has certain rights in the invention.

BACKGROUND OF THE INVENTION

Hair transplantation is a procedure that involves implanting multiple hair follicles or follicular units, from a donor site of a donor, into a recipient site of a patient. This procedure is generally done by first identifying a hair follicle in the donor site, coring around the hair follicle, and removing the hair follicle from the donor site. Then, a small opening is created in the recipient site. After the small opening has been created the hair follicle is implanted within the opening, and the opening is allowed to heal around the implanted hair follicle.

Presently, this procedure is generally performed using differing tools for extraction of the hair follicle, creation of the small opening, and implantation of the hair follicle. Further, the procedure is typically done by implanting a single hair follicle at a time. A single hair transplant session may implant anywhere from 1,500 to 3,000 hair follicles. With each hair follicle taking as long as twenty seconds to transplant, each session is very labor intensive and can last as long as eight to ten hours. As such, the current process for hair transplantation is tedious, time-consuming, and costly.

SUMMARY

The present disclosure overcomes the above and other drawbacks by providing systems and methods for hair transplants using a hair transplant device that can extract a hair follicle from a donor site, create an opening in a recipient site, and implant the hair follicle within the opening in the recipient site. The systems and methods of the present disclosure are capable of extracting multiple hair follicles from the donor site simultaneously, creating multiple openings in the recipient site simultaneously, and implanting multiple hair follicles within the multiple openings in the recipient site. This process may be done, in some implementations, simultaneously. As such, systems and methods are provided for improved hair transplant procedures that increase extraction speed, opening speed, and implantation speed, thereby increasing efficacy and reducing cost.

In accordance with one aspect of the disclosure, a hair transplant device is provided. The hair transplant device comprises a coring needle, a splitting needle, a housing, and a user interface, the coring needle forms a coring lumen configured to extract a hair follicle from a donor site. The splitting needle is configured to create an opening in a recipient site. The housing at least partially surrounds one of the coring needle and the splitting needle. The user interface extends from the housing and is movable relative to the coring needle to push the hair follicle from the coring lumen into the opening in the recipient site formed by the splitting needle.

In accordance with another aspect of the disclosure, a hair transplant device is provided. The hair transplant device comprises a coring needle, a housing, and a user interface. The coring needle forms a coring lumen configured to extract a hair follicle from a donor site of a donor. The coring needle has a distal cutting end configured to move between an opened position and a closed position based on a heat memory of a material of the distal cutting end. The housing at least partially surrounds the coring needle. The user interface extends from the housing and is movable relative to the coring needle to push the hair follicle from the coring lumen into a recipient site of a subject.

In accordance with another aspect of the disclosure, a hair transplant system is provided. The hair transplant system comprises a matrix arranging a plurality of hair transplant devices to perform multiple extractions and implantations of hair follicles in a coordinated manner. Each of the plurality of hair transplant devices comprises a coring needle, a needle, and a user interface. The coring needle forms a coring lumen configured to extract a hair follicle from a donor site of a subject. The needle is configured to create an opening in a recipient site of the subject. The user interface is movable relative to the coring lumen to implant the hair follicle within the recipient site by pushing the hair follicle from within the coring lumen into the opening in the recipient site.

In accordance with another aspect of the disclosure, a method of performing a hair transplant procedure using an automated transplant device is provided. The method comprises engaging a user interface device to cause a coring needle having a coring lumen to engage a donor site of a subject to arrange a hair follicle within the coring lumen of the coring needle. The method further comprises further engaging the user interface to cause a splitting needle to create an opening within a recipient site of the subject. The method further comprises further engaging the user interface to displace the hair follicle from the coring lumen to implant the hair follicle within the opening in the recipient site.

In accordance with another aspect of the disclosure, a method of performing a hair transplant procedure using a hair transplant device and a mold is provided. The method comprises engaging a user interface device to cause a coring needle having a coring lumen to engage a donor site of a donor to arrange a hair follicle within the coring lumen of the coring needle. The method further comprises further engaging the user interface to displace the hair follicle from the coring lumen into a mold. The method further comprises molding a biomaterial around the hair follicle to form a biomaterial mold containing the hair follicle. The method further comprises implanting the biomaterial mold containing the hair follicle within a recipient site of a subject.

The foregoing and other advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 5A is a cross-sectional view of the hair transplant device of FIG. 1, shown above a recipient site and containing a hair follicle, with a splitting needle advanced during an opening procedure.

FIG. 5B is a cross-sectional view of the hair transplant device of FIG. 5A, shown containing the hair follicle and creating an opening within the recipient site during the opening procedure.

FIG. 6A is a cross-sectional view of the hair transplant device of FIG. 1, shown containing a hair follicle and inserted into a recipient site.

FIG. 6B is a cross-sectional view of the hair transplant device of FIG. 6A, shown with a user interface advanced to implant the hair follicle within the recipient site during the implantation procedure.

FIG. 6C is a cross-sectional view of the hair transplant device of FIG. 6B, shown removed from the recipient after implanting the hair follicle during the implantation procedure.

FIG. 7A is a cross-sectional view of the hair transplant device of FIG. 1 extracting a hair follicle at a non-normal angle.

FIG. 7B is a cross-sectional view of the hair transplant device of FIG. 1 creating an opening in a recipient site at a non-normal angle.

FIG. 20A is a cross-sectional view of a hair transplant device in accordance with the present disclosure, shown containing a hair follicle and creating an opening with a splitting needle in a recipient site during an opening procedure.

FIG. 20B is a cross-sectional view of the hair transplant device of FIG. 20A, shown with a coring needle advanced, forcing the splitting needle to open.

DETAILED DESCRIPTION OF THE INVENTION

Figure 1:
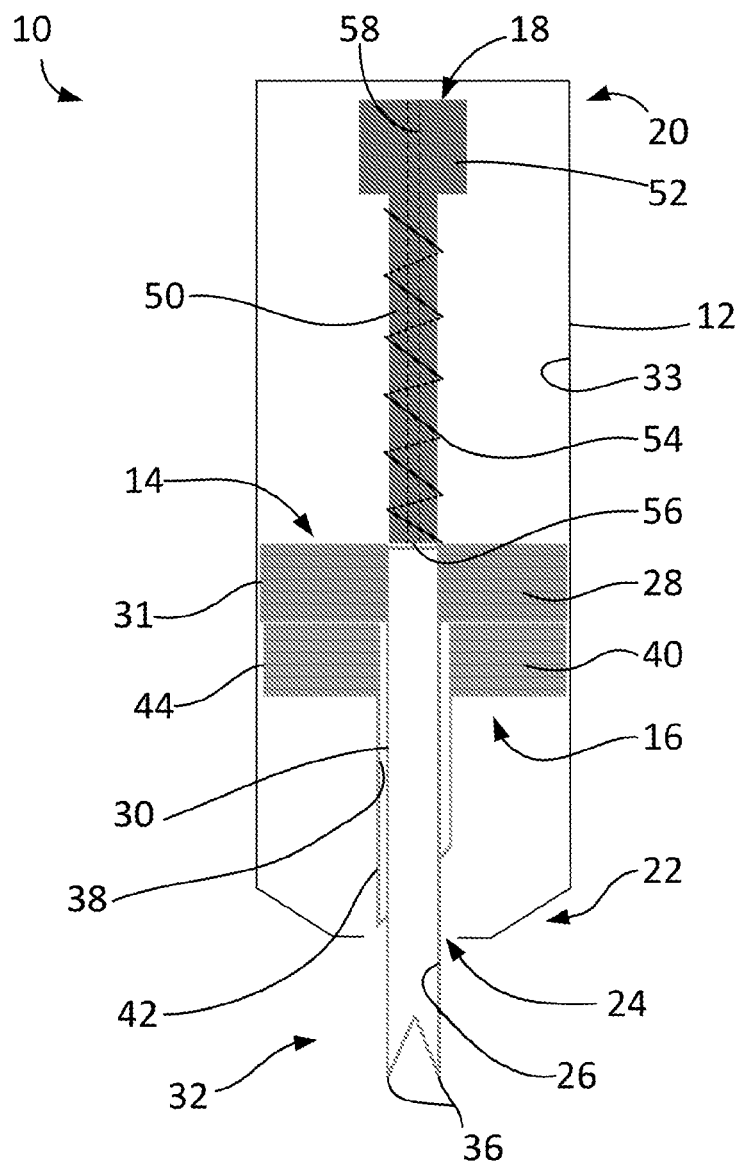
FIG. 1 is a cross-sectional view of one example of a hair transplant device in accordance with the present disclosure.

Referring to FIG. 1, a hair transplant device 10 for extracting hair follicles from a donor site of a donor and implanting them into a recipient site of a patient is illustrated. These hair follicles, or follicular units, can contain a single hair or multiple hairs grouped together. As can be seen in the illustration of FIG. 1, the hair transplant device 10 includes a housing 12 containing a coring element 14, a splitting element 16, and a user interface 18.

The housing 12 extends between a proximal end 20 and a distal end 22. The housing 12 includes an opening 24 in the distal end 22. In some instances, the housing 12 may taper toward the distal end 22, as illustrated in FIG. 1. In other instances, the housing 12 may alternatively have a distal end 22 that is round, flat, or any other suitable shape.

As will be further described, the housing 12 may be configured for connection with an automated system, such as, for example a computer-aided manufacturing (CAM) system, for automated use of the hair transplant device 10. As will also be described, the housing 12 may additionally be configured for connection with several other similar hair transplant devices, such that an array of hair transplant devices similar to the hair transplant device 10 is provided to allow for automated extraction and/or implantation of multiple hair follicles in series or simultaneously. In some instances, the housing 12 may additionally or alternatively be configured for manual manipulation (e.g., can include a handle).

The coring element 14 is disposed within the housing 12 proximate the distal end 22. The coring element 14 includes a central lumen 26 extending axially through both a coring element flange 28 and a coring needle 30. The central lumen 26 is centrally disposed within and may extend through the coring element 14, from a proximal surface of the coring element flange 28 through a distal end of the coring needle 30. The coring element flange 28 extends radially outward at a proximal end of the coring element 14, terminating at an outer surface 31. The outer surface 31 of the coring element flange 28 slidably engages an inner surface 33 of the housing 12.

Figure 2:
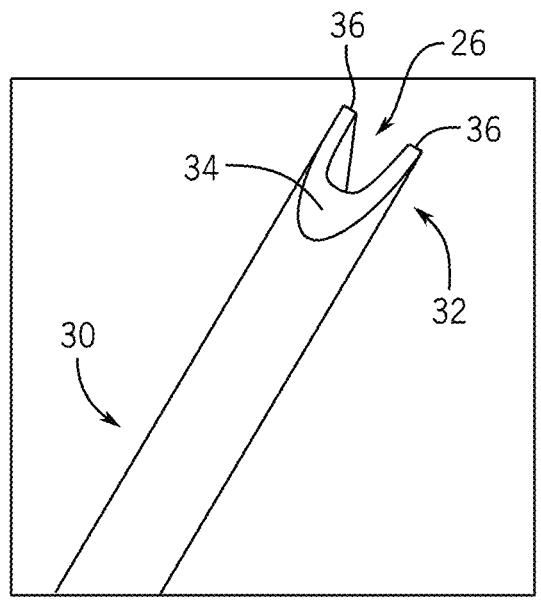
FIG. 2 is a detail view of a coring needle for use with the hair transplant device of FIG. 1.

The coring needle 30 extends distally from a distal surface of the coring element flange 28, beyond the opening 24 in the distal end 22 of the housing 12. As best illustrated in FIG. 2, the coring needle 30 may be formed as a hollow needle, with the central lumen 26 extending therethrough. Further, the coring needle 30 may include a distal cutting portion 32. The distal cutting portion 32 may be disposed completely outside of the housing 12 and include a pair of angled surfaces 34 that angle toward each other, intersecting at the distal end of the coring needle 30. Accordingly, the pair of angled surfaces 34 form a pair of cutting edges 36 disposed on opposite sides of the central lumen 26. The pair of cutting edges 36 are effectively aligned across the coring needle 30, such that they both extend radially from an inner surface of the coring needle 30 to an outer surface of the coring needle 30. As such, the coring needle 30 is configured to cut into tissue by driving the coring needle 30 into the tissue, without needing to rotate the coring needle 30.

The coring element 14 is movable between a retracted position (shown in FIGS. 5A-5B) and an extended position (shown in FIGS. 4A-4C and 6A-6C) and may be controlled, for example, through the user interface 18 or an automated control system, as will be described. In the extended position, the coring element 14 is moved distally relative to the housing 12 to allow for extraction of a hair follicle, as will be described below. In the retracted position, the coring element 14 is moved proximally, such that a smaller portion of the coring needle 30 extends out of the opening 24 in the distal end 22 of the housing 12.

Referring again to FIG. 1, the splitting element 16 is also disposed within the housing 12 proximate the distal end 22, partially enveloping the coring needle 30 of the coring element 14. The splitting element 16 similarly includes a central lumen 38 extending axially through a splitting element flange 40 and a splitting needle 42. The central lumen 38 is centrally disposed within and extends all the way through the splitting element 16, from a proximal surface of the splitting element flange 40 through a distal end of the splitting needle 42. The central lumen 38 of the splitting element 16 further has an inner diameter that is slightly larger than the outer diameter of the coring needle 30 of the coring element 14, such that coring needle 30 can be inserted therethrough, and the splitting element 16 can slide relative to the coring element 14 on the coring needle 30, as will be described below.

The splitting element flange 40 extends radially outward at a proximal end of the splitting element 16, terminating at an outer surface 44. The outer surface 44 of the splitting element flange 40 slidably engages the inner surface 33 of the housing 12. The splitting element flange 40 is further disposed more proximate the distal end 22 of the housing 12 than the coring element flange 28.

Figure 3:
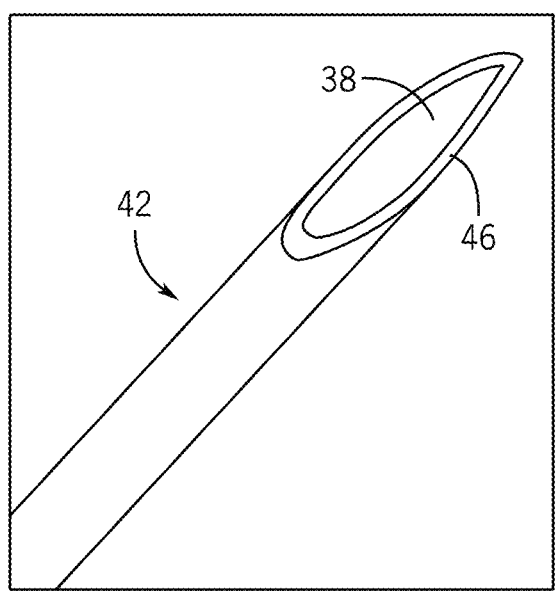
FIG. 3 is a detail view of a splitting needle for use with the hair transplant device of FIG. 1.

The splitting needle 42 is coaxially disposed around the coring needle 30 and extends distally from the splitting element flange 40. As best illustrated in FIG. 3, the splitting needle 42 is a hollow needle, with the central lumen 38 extending therethrough. Further, the splitting needle 42 includes a distal cutting edge 46 that is angled relative to a central axis of the splitting needle 42. The distal cutting edge 46 has a specific cutting geometry (e.g., the angle of the distal cutting edge 46) that controls against tissue from entering the splitting needle 42 while the splitting needle 42 cuts into skin by piercing the skin and gradually pushing the tissue apart, similar to the function of a hypodermic needle.

The splitting element 16 is movable between a retracted position (shown in FIGS. 1 and 4A-4C) and an extended position (shown in FIGS. 5A-6B) and may be controlled, for example, through the user interface 18 or an automated control system, as will be described. In the retracted position, the splitting element 16 is advance proximally such that the distal end of the splitting needle 42 is disposed within the housing 12, more proximal than the distal end of the coring needle 30. Further, in the retracted position, the proximal surface of the splitting element flange 40 may contact the distal surface of the coring element flange 28. In the extended position, the splitting element 16 is moved distally, such that a portion of the splitting needle 42 extends out of the opening 24 in the distal end 22 of the housing 12, past the distal end of the coring needle 30.

Referring again to FIG. 1, the user interface 18 is disposed to extend from the housing 12, near the proximal end 20, and is partially enveloped by the coring element 14. The user interface 18 may include a pin 50, a head 52, and a spring 54. The pin 50 extends distally from the head 52, and is disposed partially within the central lumen 26 of the coring element 14. The illustrated pin 50 includes a distal tip surface 56 that is flat. However, in some instances, the distal tip surface 56 could alternatively be round, pointed, or any other suitable shape. The head 52 extends radially outward at a proximal end of the user interface 18, past an outer diameter of the pin 50 to present a surface upon which a force or pressure can be exerted by a user to control actuation of the system. In some instances, the head 52 may be configured for connection with the automated system, such that the user interface 18 can be moved automatically. For example, in some instances, the user interface 18 can be actuated using a solenoid actuator to push the coring element 14 or the splitting element 16 through the scalp. The solenoid actuator may have enough force to drive a single or multiple elements or needles into the tissue. In other instances, the head 52 may additionally or alternatively be configured for other kinds of automated or manual manipulation.

The spring 54 is disposed around the pin 50, between a distal surface of the head 52 and the proximal surface of the coring element flange 28 of the coring element 14. The spring 54 is configured to compress when the user interface 18 is advanced distally, thereby providing a resistive force preventing the user interface 18 from entering the central lumen 26 of the coring element 14.

The user interface 18 is movable between a retracted position (shown in FIGS. 1 and 4A-5B) and an inserted position (shown in FIGS. 6A and 6B). In the retracted position, the user interface 18 is moved proximally, such that only a small portion of the pin 50 is disposed within the central lumen 26 of the coring element 14. In the inserted position, the user interface 18 is moved distally a predetermined amount, such that a majority of the pin 50 is disposed within the central lumen 26, and the distal tip surface 56 of the pin 50 is disposed proximate the distal end of the coring needle 30.

In some instances, the user interface 18 may further include a central lumen 58 extending axially from a proximal surface of the head 52 through the distal tip surface 56 of the pin 50. The central lumen 58 may be included to allow for flow of a gas or a liquid through the user interface 18. In these cases, the head 52 may be coupled to a fluid delivery system and/or a fluid aspiration system to provide gas or liquid through the user interface 18 and/or to suction gas or liquid through the user interface 18.

Now that the general structure of the hair transplant device 10 has been described above, exemplary methods of use will be described below. It should be noted that the methods of use described below are given as examples, and are not meant to be limiting in any way.

The hair transplant device 10 can be used to perform multiple different procedures to complete a hair transplant operation on a patient. For example, the device 10 is designed to perform an extraction procedure (shown in FIGS. 4A-4C); an opening procedure (shown in FIGS. 5A and 5B); and an implantation procedure (shown in FIGS. 6A and 6B). Although any one of these three procedures can be performed individually by the hair transplant device 10, the hair transplant device 10 allows for the three procedures to be done sequentially and repetitively. That is, the hair transplant device 10 can first be used to extract a hair follicle from a donor site of a donor during an extraction procedure. The hair transplant device 10 can then, while still containing the hair follicle from the donor site, be used to create an opening that is configured to receive the hair follicle in a recipient site of the patient. Then, the hair transplant device 10 can be used to implant the hair follicle from the donor site into the recipient site. Finally, once the hair follicle has been implanted into the recipient site, the hair transplant device 10 can be used to repeat this process again and again to complete the hair transplant operation. This process may be repeated, for example, tens, hundreds, or even thousands of times.

Figure 4C:
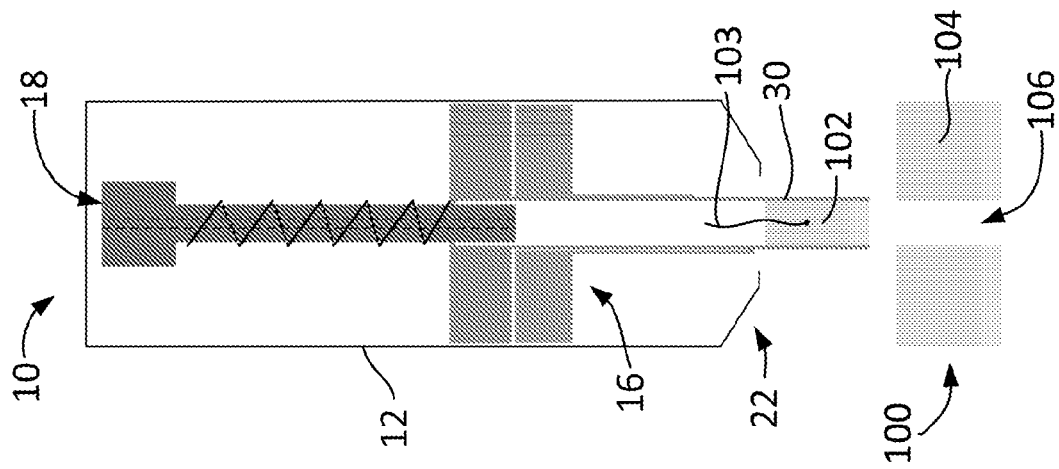
FIG. 4C is a cross-sectional view of the hair transplant device of FIG. 4B, shown with the coring needle removed from the donor site containing a hair follicle.
Figure 4B:
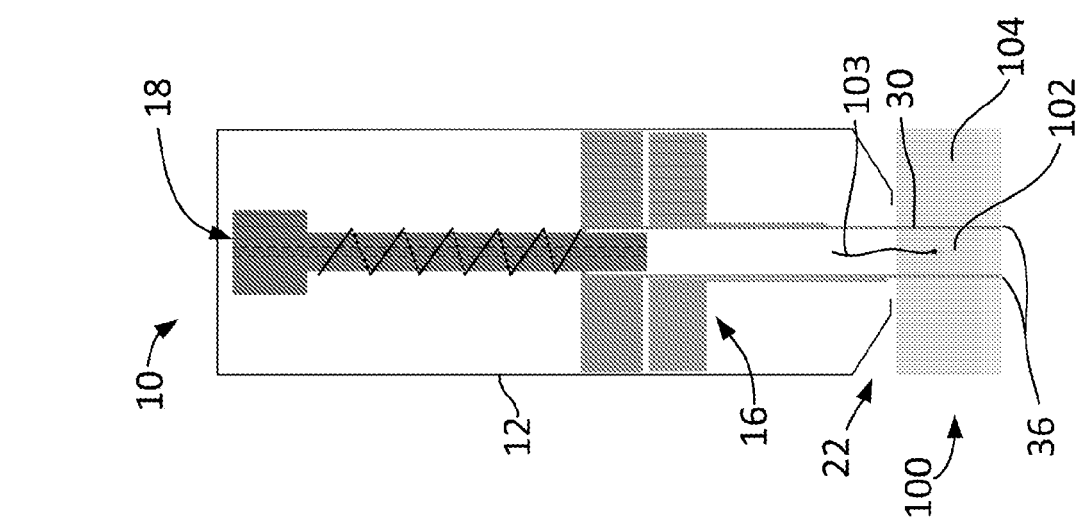
FIG. 4B is a cross-sectional view of the hair transplant device of FIG. 4A, shown with a coring needle inserted into the donor site during the extraction procedure.
Figure 4A:
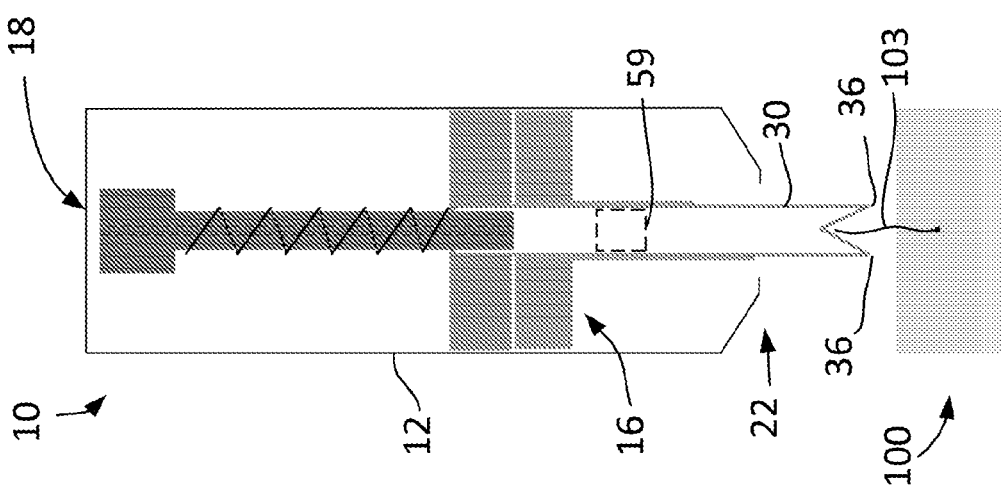
FIG. 4A is a cross-sectional view of the hair transplant device of FIG. 1, shown above a donor site during an extraction procedure.

FIGS. 4A-4C illustrate the hair transplant device 10 being used during an extraction procedure. As illustrated, the hair transplant device 10 can first be placed above a donor site 100 of a donor in an extraction position, as shown in FIG. 4A. In the extraction position, both the splitting element 16 and the user interface 18 are in the corresponding retracted positions. As such, the coring needle 30 is exposed outside of the distal end 22 of the housing 12. With the hair transplant device 10 in the extraction position, the coring needle 30 can then be inserted into the donor site 100 around a skin core 102, with the pair of cutting edges 36 cutting through the surrounding donor tissue 104, as illustrated in FIG. 4B. The central lumen 26 of the coring needle 30 may define an inner diameter that is larger than the average distance between hair follicles within the donor site 100 (i.e., approximately 1 mm). As such that the hair transplant device 10 should always extract skin cores 102 containing, along with other skin components (e.g., epidermis, collagen, elastin, blood vessels, etc.), at least one hair follicle having at least one hair 103 during the extraction procedure.

As described below, the coring needle 30 can be inserted at varying angles to extract the skin core 102 having the hair follicle in a desired orientation. This variation of the angle of insertion can be controlled using the automated system described above. After insertion, the coring needle 30 can then be removed from the donor site 100, still containing the skin core 102 within the coring needle 30, thereby leaving a small opening 106 in the donor site 100.

It should be noted that, during the extraction procedure, in the instances where the user interface 18 includes the central lumen 58 (as shown in FIG. 1), suction or negative pressure may be provided through the user interface 18 into the coring needle 30 by the fluid aspiration system when removing the coring needle 30 to provide additional control and force for removing the skin core 102 from the donor site 100. In these instances, a porous stop 59 (shown in FIG. 4A) may be incorporated into the needle bore to prevent the skin core 102 from being drawn too far into the coring needle 30. Said differently, the porous stop 59 is configured to prevent the skin core 102, potentially containing a hair follicle, from being drawn past a predetermined position within the coring needle 30.

FIGS. 5A and 5B illustrate the hair transplant device 10 being used during an opening procedure. As illustrated, the hair transplant device 10 can first be placed above a recipient site 200 of a recipient in an opening position, as shown in FIG. 5A. In the opening position, the user interface 18 remains in the retracted position, but the splitting element 16 is moved into the extended position. As such, the distal end of the splitting needle 42 is extended slightly past the distal end of the coring needle 30. With the hair transplant device 10 in the opening position, the splitting needle 42 (and also the coring needle 30) can be inserted into the recipient site 200, with the distal cutting edge 46 forming an opening in the tissue 202, thereby creating a small opening 204 in the recipient site 200. Notably, though illustrated as creating this small opening 204 at an angle that is normal to a surface of the recipient site 200, the small opening 204 may be formed at an angle that is non-normal. Such non-normal angles may be facilitated by angling surfaces of the splitting needle 42 and/or orienting the splitting needle 42 to engage the recipient site 200 at a non-normal angle, as described below.

FIGS. 6A and 6B illustrate the hair transplant device 10 being used during an implantation procedure. As illustrated, with the distal ends of both the splitting needle 42 and the coring needle 30 inserted into the small opening 204 created during the opening procedure, and the skin core 102 disposed within the coring needle 30, the hair transplant device 10 can be moved into the implantation position. In the implantation position, the splitting element 16 can remain in the extended position, and the user interface 18 can be moved into the inserted position. While the user interface 18 is moved into the inserted position, the pin 50 eventually comes into contact with the skin core 102, thereby pushing the skin core 102 out of the coring needle 30, into the small opening 204. As such, the depth of the implantation of the skin core 102 into the small opening 204 can be controlled by the predetermined amount that the user interface 18 is moved distally. After the skin core 102 has been pushed out of the coring needle 30, into the small opening 204, the splitting needle 42 and the coring needle 30 can be removed from the small opening 204, leaving the skin core 102 having the hair follicle implanted therein.

In some instances, the user interface 18 may be configured to remain in contact with the skin core 102 while the coring needle 30 and the splitting needle 42 are withdrawn from the recipient site 200. Specifically, in these instances, the user interface 18 may be long enough to protrude distally out of both the coring needle 30 and the splitting needle 42 when they are moved into their corresponding retracted positions within the hair transplant device 10. As such, the user interface 18 can provide pressure to the skin core 102 to keep the skin core 102 within the opening 204 while the coring needle 30 and the splitting needle 42 are withdrawn. In some cases, the pressure from the user interface 18 can be maintained for an extended period of time (e.g., one to two minutes) to aid in the reduction of bleeding from the recipient site 200.

Similar to the extraction procedure above, the skin core 102 can be implanted at various angles to create a more natural hair appearance in the recipient site by implanting the skin core 102 having the hair follicle in a desired orientation, as described below.

Figure 7C:
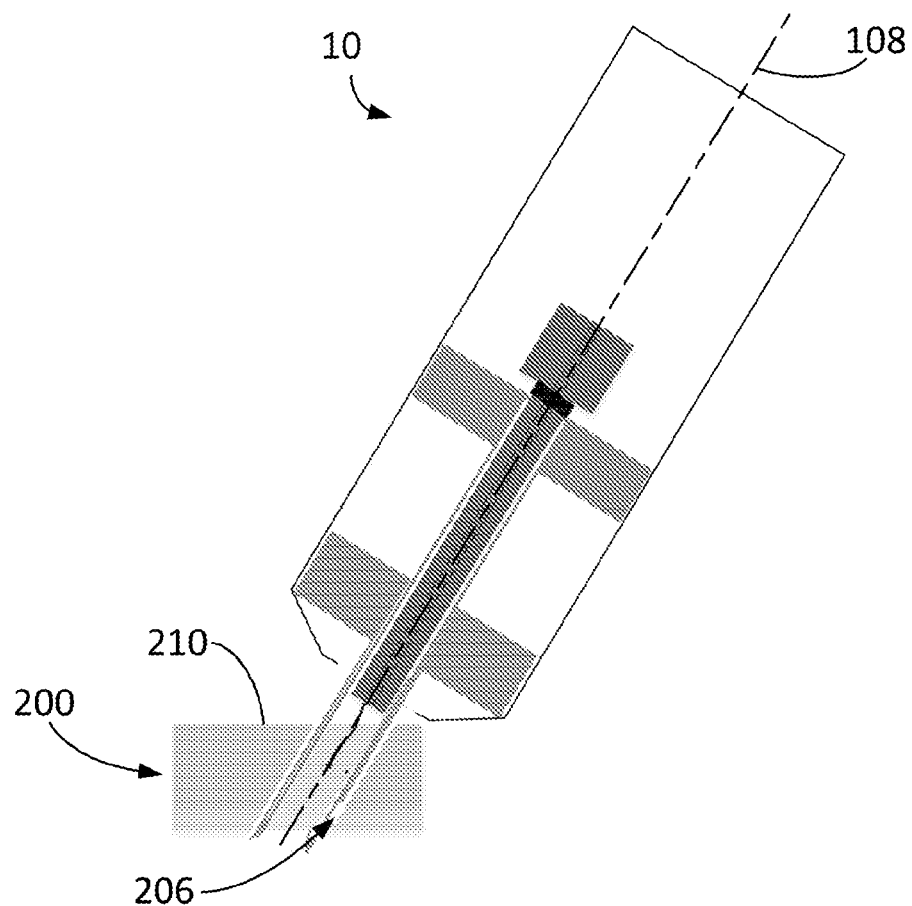
FIG. 7C is a cross-sectional view of the hair transplant device of FIG. 1 implanting a hair follicle at a non-normal angle.

As shown in FIGS. 7A-7C, any of extraction, splitting, and/or implantation may be performed at angles that are non-normal to the extraction or donor sites. Said differently, the hair transplant device 10 can be used to extract the skin core 102 with the central lumen 26 of the coring element 14 aligned with a hair follicle axis 108 (i.e., an axis of orientation of the hair 103 of the hair follicle) that is not normal to a skin surface 110 of the donor site 100 (as shown in FIG. 7A). The hair transplant device 10 can further be used to create an angled opening 206 that is not normal to a skin surface 210 of the recipient site 200 (as shown in FIG. 7B). Then, the hair transplant device 10 can be used to insert the skin core 102, within the angled opening 206, with the hair follicle axis 108 at an angle that is not normal to the skin surface 210 (as shown in FIG. 7C).

Once implanted, the hair 103 of the hair follicle will grow in the direction of the hair follicle axis 108. As such, extracting the skin core 102 with the central lumen 26 of the coring element 14 aligned with the hair follicle axis 108 allows the skin core 102 to be implanted such that the hair 103 will grow at a known angle relative to the skin surface 210 of the recipient site 200. Accordingly, the skin core 102 can be implanted at varying angles to produce a natural-looking hair line in the recipient site 200. In some instances, the skin cores 102 can be extracted and/or implanted at angles of up to 60 degrees relative to the donor site 100 and/or the recipient site 200.

For example, these non-normal orientations may be facilitated by the arrangement of cutting surfaces and/or arrangement of the device relative to the subject. In fully automated implementations, angle control or selection can be controlled by the automated system described above. In manual implementations, device selection from among different devices with differing geometries and/or user orientation of device during the process may control angle selection.

Further, during the implantation procedure, in the instances where the user interface 18 includes the central lumen 58 (as shown in FIG. 1), positive pressure may be provided through the user interface 18 into the coring needle 30 by the fluid delivery system to provide additional control and force for pushing the skin core 102 out of the coring needle 30. Additionally or alternatively, during the implantation procedure, various fluids can be provided through the central lumen 58 of the user interface 18 into the coring needle 30 by the fluid delivery system to assist in procedures, therapy, and biology related to the implantation of hair follicles. These fluids can be any of lubricants, flushing fluids, cleansing fluids, anesthesia fluids, medicinal fluids, or any other fluids desired to be applied through the coring needle 30.

For example, in some instances, during an extraction procedure, the hair transplant device 10 can be used to inject a saline solution under the donor site 100 to make the hair follicles stand up more normal to the donor site 100. In some other instances, the hair transplant device 10 can be used to apply tumescent anesthesia to the donor site 100.

Figure 8B:
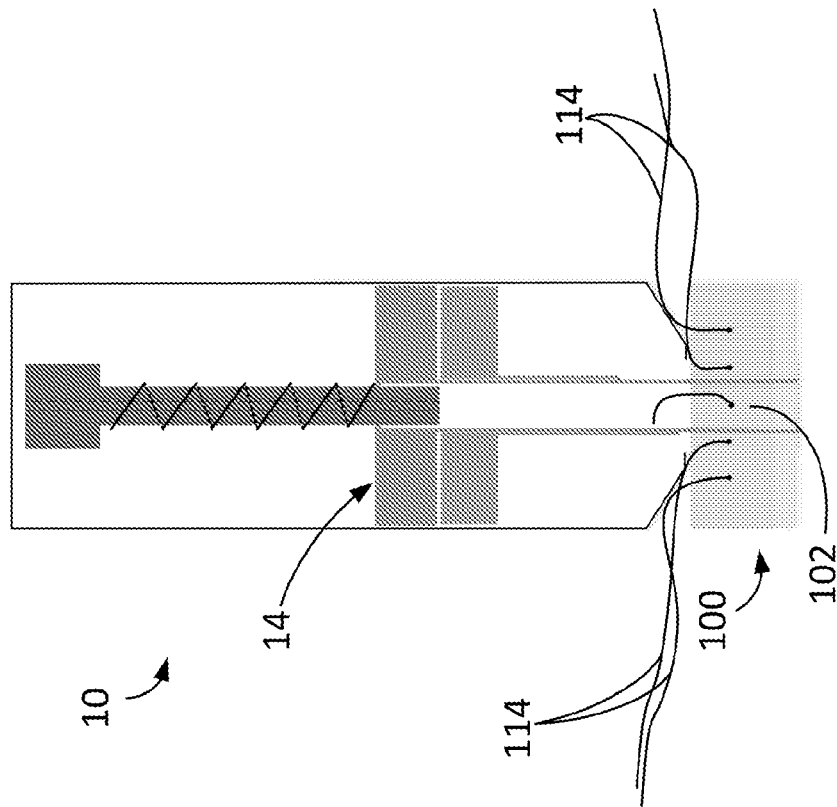
FIG. 8B is a cross-sectional view of the hair transplant device of FIG. 8A, shown extracting a hair follicle from an untrimmed donor site.
Figure 8A:
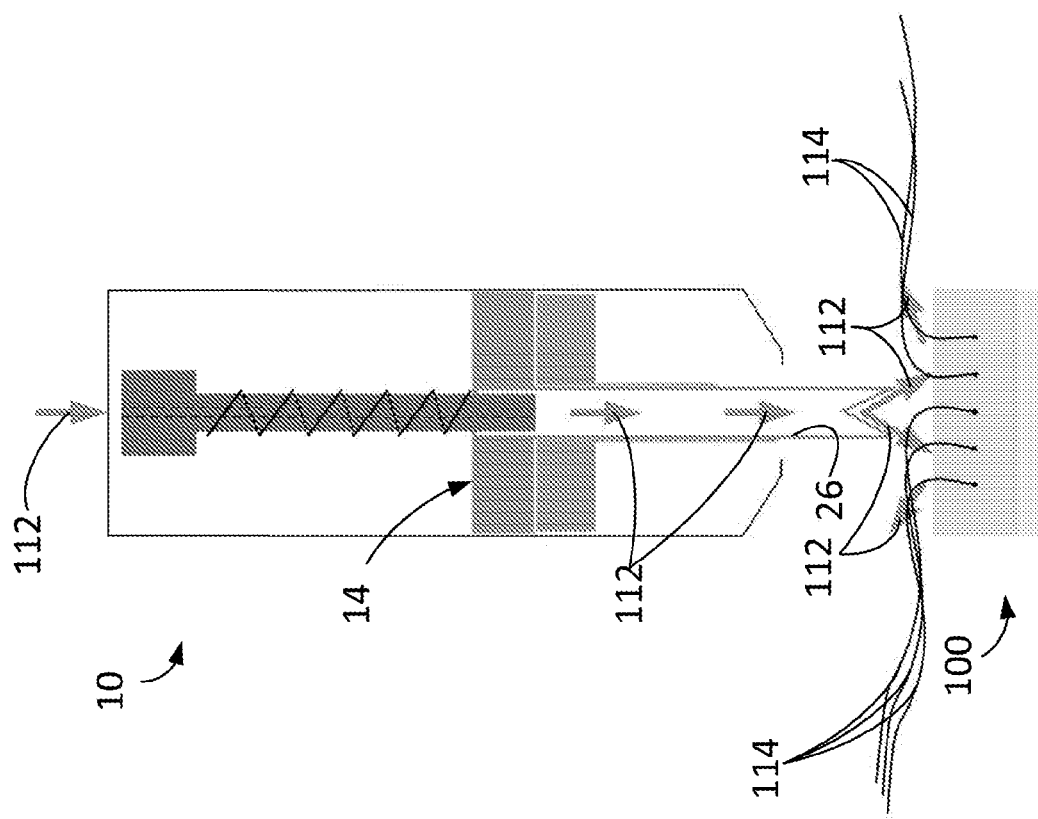
FIG. 8A is a cross-sectional view of the hair transplant device of FIG. 1, shown above a donor site with a fluid flow through the hair transplant device forcing a plurality of hair follicles to bend away from the hair transplant device.

Further, as shown in FIGS. 8A and 8B, the fluid delivery system can continuously push a flow (signified by arrows 112) of fluid (e.g., air) through the central lumen 26 of the coring element 14 to blow any long hairs 114 of the donor site 100 away from the hair transplant device 10 (as shown in FIG. 8A). With the long hairs 114 blown away from the coring element 14, the coring element 14 can be used to extract the skin core 102 (as shown in FIG. 8B), as described above with reference to FIGS. 4A-4C. By blowing the long hairs 114 away from the hair transplant device 10, the hair transplant device 10 is capable of extracting a skin core 102 containing a hair follicle from the donor site 100, without needing to first trim or clip the long hairs 114.

Figure 9:
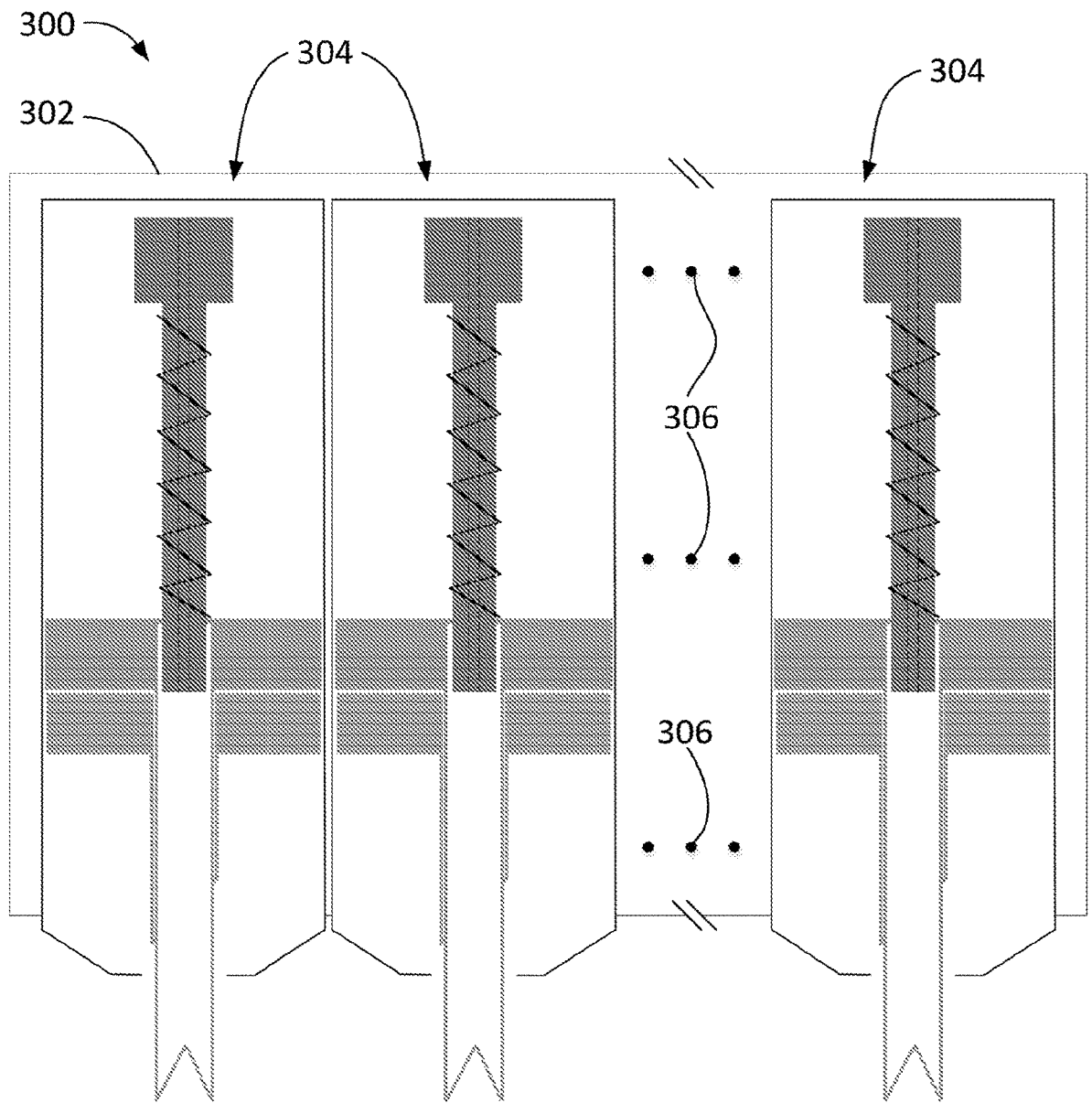
FIG. 9 is a cross-sectional view of an array of hair transplant device in accordance with the present disclosure.

Referring now to FIG. 9, a hair transplant device 300 for extracting tens, hundreds, or thousands of hair follicles simultaneously from a donor site of a donor and then implanting the tens, hundreds, or thousands of hair follicles simultaneously into a recipient site of a patient is illustrated. As can be seen in the illustration of FIG. 9, the hair transplant device 300 includes a body 302 containing a plurality of hair transplant devices 304. Each of the plurality of hair transplant devices 304 work identically to the hair transplant device 10 described above.

As illustrated, there are two hair transplant device 304 separated from a third hair transplant device 304 by three sets of ellipses 306. The ellipses 306 illustrate that the hair transplant device 300 can include any number of hair transplant devices 304 desired for a given hair transplant operation. For example, the hair transplant device 300 can include a two dimensional array of including tens, hundreds, or thousands of hair transplant devices 304 configured to allow for the simultaneous extraction of tens, hundreds, or thousands of hair follicles from a donor site, the simultaneous opening of tens, hundreds, or thousands of small openings on a recipient site, and the simultaneous implantation of tens, hundreds, or thousands of hair follicles within a recipient site.

The hair transplant device 300 can again be configured for use with an automated system, as will be described below. As such, the angle, distribution, and separation between the plurality of hair transplant devices 304 can be controlled by the automated system to effectively control the angle, distribution, and separation between simultaneous extractions, such that every one of the plurality of hair transplant devices 304 extracts an aligned hair follicle. Similarly, the angle, distribution, and separation between the plurality of hair transplant devices 304 can be controlled by the automated system to effectively control the angle, distribution, and separation between simultaneous implantations.

Figure 10:
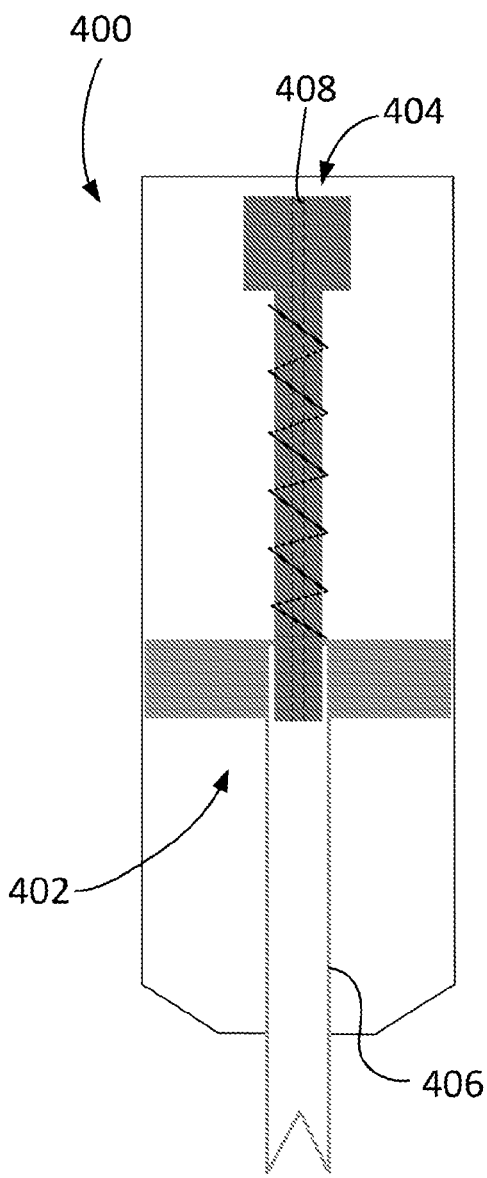
FIG. 10 is a cross-sectional view of a coring device in accordance with the present disclosure.
Figure 11:
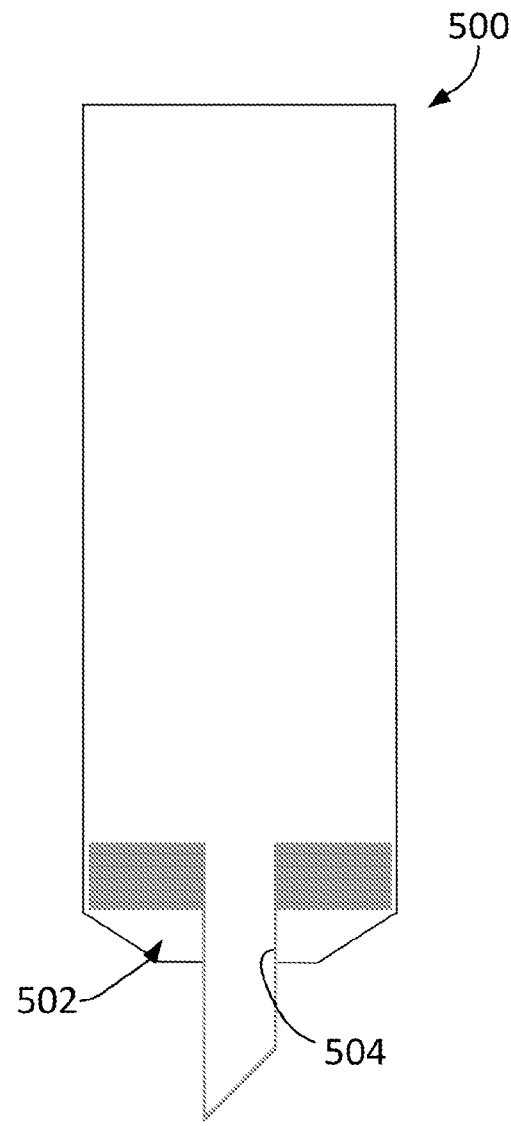
FIG. 11 is a cross-section view of a splitting device in accordance with the present disclosure.

Referring now to FIG. 10, a coring device 400 having a coring element 402, or an array of coring elements, similar to the coring element 14 described above, and a user interface 404 (or an array of corresponding pin components), similar to the user interface 18 described above, may be used to extract a hair follicle (or multiple hair follicles). Again, the user interface 404 can be hollow, including a central lumen 408. Then, the coring element 402 can be positioned behind a separate splitting device 500 (as shown in FIG. 11) including a splitting element 502 (or a corresponding array of splitting elements), similar to the splitting element 16 described above. The splitting device 500 can be used to create a small opening in a recipient site, as also described above. It should be noted that either of the coring device 400 or the splitting device 500 can be configured to engage the automated system, the fluid delivery system, or the fluid aspiration system described above, for similar uses to those described above with reference to the hair transplant device 10.

In some instances, a coring needle 406 of the coring element 402 can then be inserted through a central lumen 504 of the splitting element 502 to implant the hair follicle into the small opening created in the recipient site by the splitting element 502. However, in the case that the central lumen 504 of the splitting element 502 is not large enough for the coring element 402 to fit through, with the coring element 402 positioned behind the splitting element 502, the user interface 404 can be configured to push the hair follicle into and through the central lumen 504 of the splitting element 502, into the small opening in the recipient site.

Figure 12:
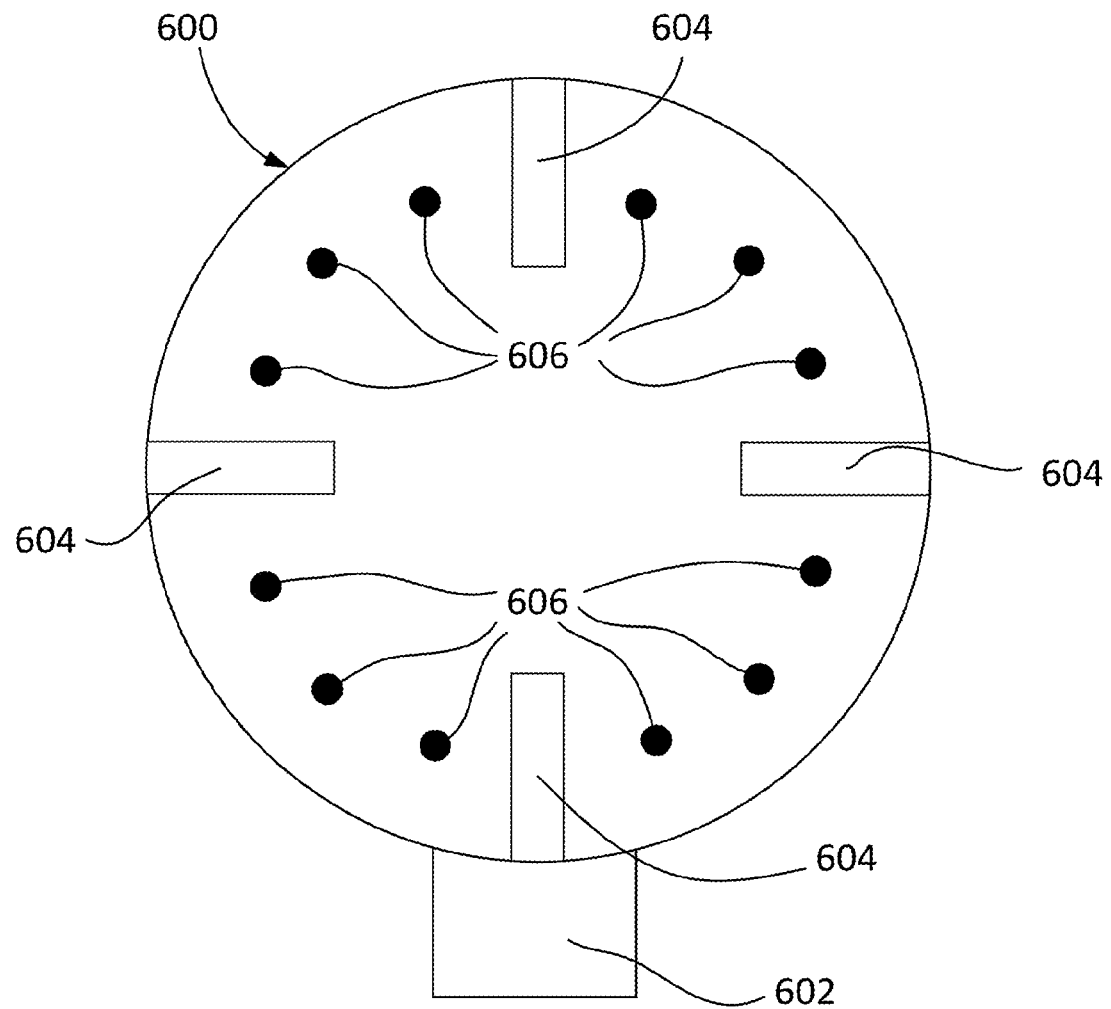
FIG. 12 is a plan view of a rotating chamber container configured for use with the devices of FIGS. 8 and 9.

Referring to FIG. 12, a rotating chamber container 600 for loading and dispensing hair follicles is illustrated. The rotating chamber container 600 includes a device port 602 and a plurality of hair follicle chambers 604. As illustrated, the rotating chamber container 600 includes four evenly spaced hair follicle chambers 604. However, as signified by ellipses 606 spanning between each adjacent hair follicle chamber 604, the rotating chamber container 600 can include any number of evenly or unevenly spaced hair follicle chambers 604. The device port 602 is rotatably coupled to the rotating chamber container 600 and configured to engage either of the coring device 400 or the splitting device 500 described above, thereby selectively coupling either of the coring device 400 or the splitting device 500 to the rotating chamber container 600.

As such, during a hair transplant operation, the coring device 400 can first be attached to the rotating chamber container 600 using the device port 602. With the coring device 400 attached to the rotating chamber container 600, the coring element 402 can then be used to extract a hair follicle from a donor site, as described above. After the coring element 402 has extracted a hair follicle from a donor site, suction can be applied through the central lumen 408 of the user interface 404 to move the hair follicle up, through the device port 602, and into one of the hair follicle chambers 604, thereby loading the hair follicle chamber 604. Once the hair follicle chamber 604 has been loaded with the hair follicle, the rotating chamber container 600 can be rotated to align the device port 602 with the next unloaded hair follicle chamber 604. The coring device 400 can then similarly be used to load that hair follicle chamber 604. This process can be repeated until a desired number (or every one) of the hair follicle chambers 604 of the rotating chamber container 600 has been loaded.

Once the desired number (or every one) of the hair follicle chambers 604 has been loaded, the coring device 400 can be detached from the rotating chamber container 600, and the splitting device 500 can similarly be attached to the rotating chamber container 600 using the device port. With the splitting device 500 attached to the rotating chamber container 600, the splitting element 502 can be used to create a small opening in a recipient site, as described above. Then, positive pressure can move the hair follicle from a hair follicle chamber 604, through the central lumen 504 of the splitting element 502, and into the small opening, thereby implanting the hair follicle within the recipient site. This process can repeated several times until every hair follicle within the loaded hair follicle chambers 604 has been implanted into the recipient site.

Figure 13:
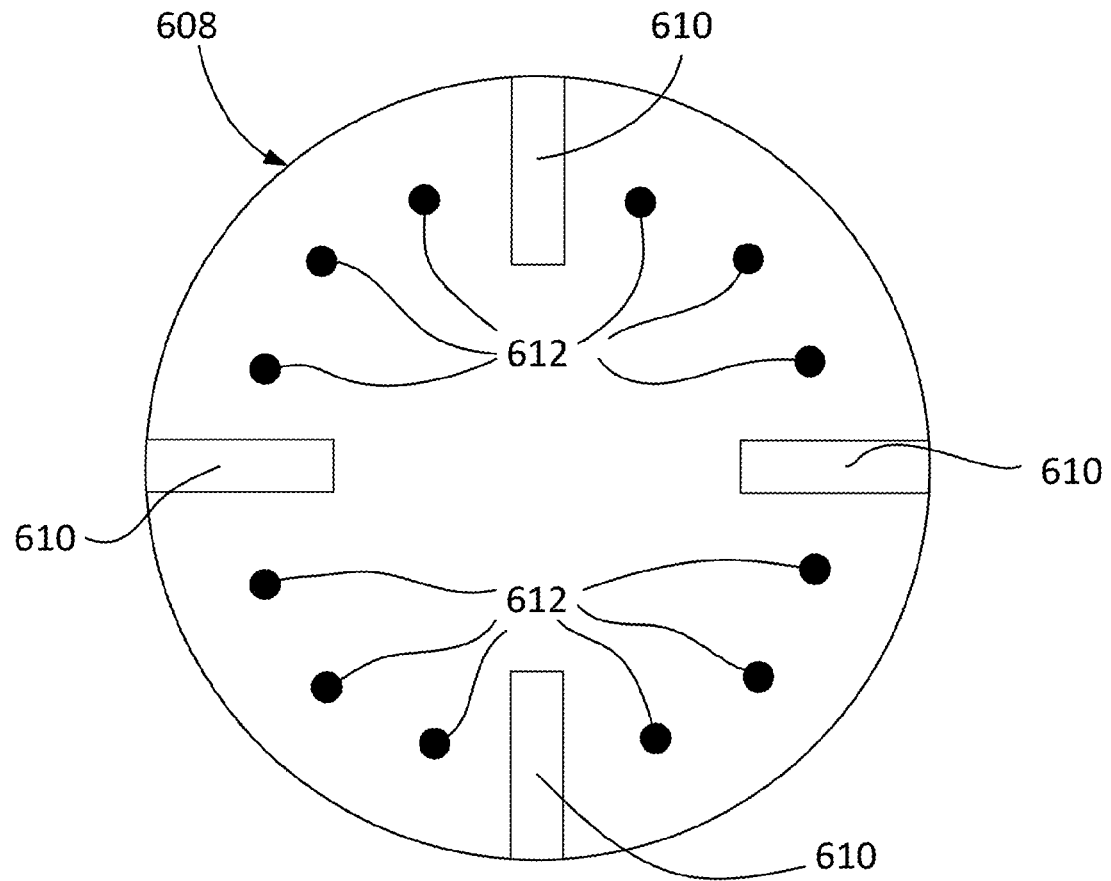
FIG. 13 is a plan view of a rotating container configured for use with the hair transplant device of FIG. 1.

Referring now to FIG. 13, an alternate rotating container 608 is illustrated. The rotating container 608 is similar to the rotating chamber container 600, but instead of having a plurality of hair follicle chambers 604, it has a plurality of hair transplant devices 610. The hair transplant devices 610 are substantially similar to the hair transplant device 10 described above. As illustrated, there are four hair transplant devices 610. However, again, ellipses 612 are shown between the hair transplant devices 610 to signify that there could be any number of evenly or unevenly spaced hair transplant devices 610 disposed around the circumference of the rotating container 608.

The hair transplant devices 610 of the rotating container 608 can be used to extract a plurality of skin cores containing hair follicles from a donor site, as described above with respect to the hair transplant device 10. As such, the rotating container 608 can first extract a first skin core having a first hair follicle with a first hair transplant device 610. Then the rotating container 608 can be rotated, and a second skin core having a second hair follicle can be extracted using a second hair transplant device 610. This can be repeated until the rotating container 608 is loaded (i.e., each of the hair transplant devices 610 contains a skin core having a hair follicle).

Once the rotating container 608 is loaded, the hair transplant devices 610 of the rotating container 608 can similarly be used to implant the skin cores having the hair follicles within a recipient site, as described above with respect to the hair transplant device 10. As such, the rotating container 608 can create a first opening using the first hair transplant device 610, and can subsequently implant the first skin core from the first hair transplant device 610 within the first opening. The rotating container 608 can then be rotated and used to create a second opening with the second hair transplant device 610. Subsequently, the rotating container 608 can implant the second skin core from the second hair transplant device 610 within the second opening. This can be repeated until the rotating container 608 is unloaded (i.e., each of the skin cores within the hair transplant devices 610 have been implanted into the recipient site).

As such, the rotating container 608 can be operated in this manner (i.e., loading and unloading the rotating container 608) repetitively to complete a hair transplant procedure.

Figure 14:
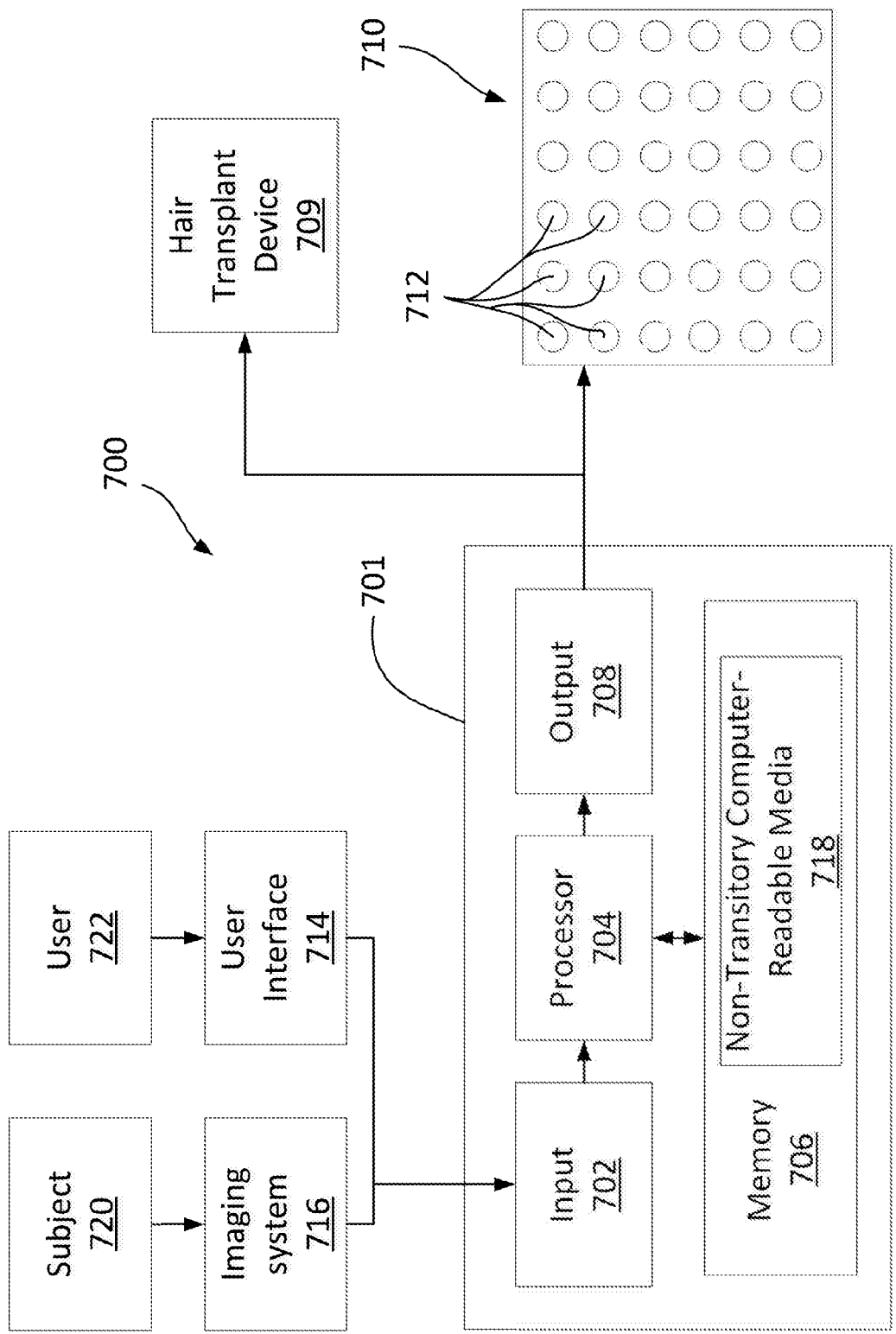
FIG. 14 is a schematic diagram of a hair transplant system in accordance with the present disclosure.

Referring to FIG. 14, a block diagram of an exemplary automated hair transplant system 700 configured to operate any of the hair transplant devices described herein is shown. In general, the hair transplant system 700 may include a controller 701 having one or more inputs 702, processors 704, memories 706, and outputs 708, and may be configured to operate a single hair transplant device 709 and/or a matrix 710 of hair transplant devices 712 to carry out steps for extracting hair follicles from a donor site, creating an opening in a recipient site, and implanting the hair follicles in the recipient site. The hair transplant devices 709, 712 can include, for example, any of the hair transplant devices 10, 300, 400, 500 described above.

The hair transplant system 700 may include, access, or communicate with one or more user interfaces 714 and/or an imaging system 716, by way of a wired or wireless connection to the inputs 702. In various implementations, the hair transplant system 700 may include any computing device, apparatus or system configured for carrying out instructions and providing input/output capabilities, and may operate as part of, or in collaboration with other computing devices and sensors/detectors (local and remote). In this regard, the hair transplant system 700 may be a system that is designed to integrate a variety of software and hardware capabilities and functionalities, and/or may be capable of operating autonomously. In addition, in various configurations, the components illustrated in FIG. 14 may be implemented using multiple separate components, and similarly, multiple illustrated components can be combined into one component.

The input 702 may include any one or more different input elements, such as a mouse, keyboard, touchpad, touch screen, buttons, and the like, for receiving various selections and operational instructions from a user through touch, movement, speech, etc. The input 702 may also include various drives and receptacles, such as flash-drives, USB drives, CD/DVD drives, and other computer-readable medium receptacles, for receiving various data and information. To this end, input 702 may also include various communication ports and modules, such as Ethernet, Bluetooth, or Wi-Fi, for exchanging data and information with these, and other external computers, systems, devices, machines, mainframes, servers or networks.

In addition to being configured to carry out various steps for operating the hair transplant system 700, the processor 704 may be configured to execute instructions, stored in the memory 706 in a non-transitory computer-readable media 718. The instructions executable by the processor 704 may correspond to various instruction for completing a hair transplant procedure. Although the non-transitory computer-readable media 718 is shown in FIG. 14 as included in the memory 706, it may be appreciated that instructions executable by the processor 704 may be additionally or alternatively stored in another data storage location having non-transitory computer-readable media.

In some aspects, the processor 704 may be configured to receive and process image data from a subject 720, such as a donor or a recipient, captured by the imaging system 716 to identify hair follicles and hair follicle orientations within a donor site of the donor and/or to determine implantation locations and necessary implantation angles within a recipient site of the recipient. In some aspects, the processor 704 may access information and data, including video signals, stored in or emitted by the imaging system 716 and/or the user interface 714. In some aspects, the imaging system 716 may acquire either a single image or a continuous video signal using, for example, a camera, an infrared scanning system, or any other image capturing or video recording device that can be used to periodically image and/or scan and/or continuously record the subject 720.

The output 708 of the hair transplant system 700 is configured to effectuate the operation of the matrix 710 of hair transplant devices 712. As such, the output 708 may include various robotic devices capable of manipulating and operating the hair transplant devices 712 to effectuate extraction of hair follicles from a donor site, creation of openings within the recipient, and implantation of the hair follicles within the openings of the recipient, as described above, with reference to any of the hair transplant devices 10, 300, 400, 500, 600. The hair transplant devices 712 can be disposed between approximately 0.5 mm and 1.5 mm away from each other to provide a natural-looking hair implant disbursement.

As such, a user 722, such as a doctor or other hair transplant procedure personnel, can interact with the user interface 714 to command the automated hair transplant system 700 to effectuate a hair transplant procedure on a subject 720 in accordance with any of the devices and methods described herein.

Figure 16:
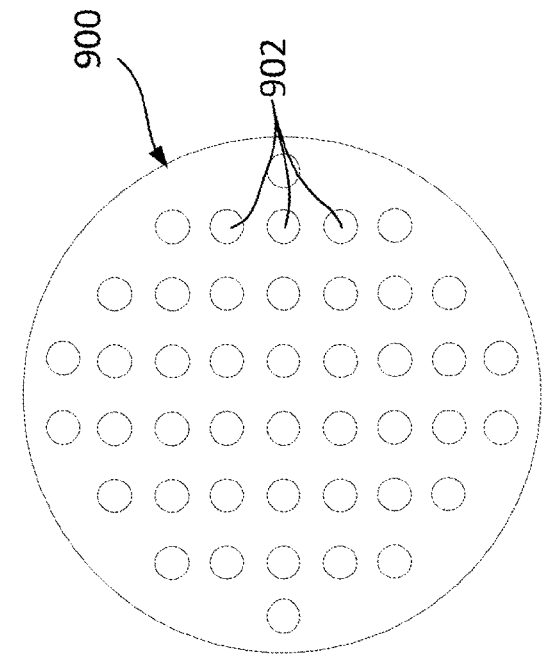
FIG. 16 is a plan view of a circular array of hair transplant devices in accordance with the present disclosure.
Figure 17:
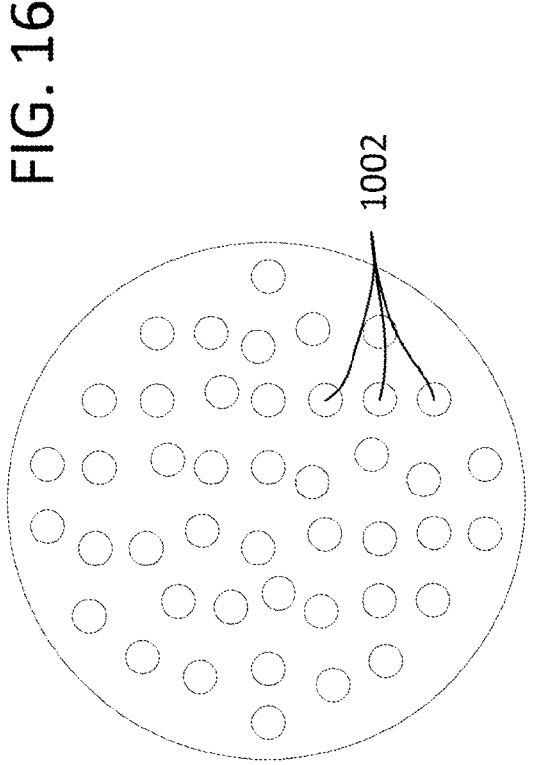
FIG. 17 is a plan view of a circular array of unevenly dispersed hair transplant devices in accordance with the present disclosure.
Figure 15:
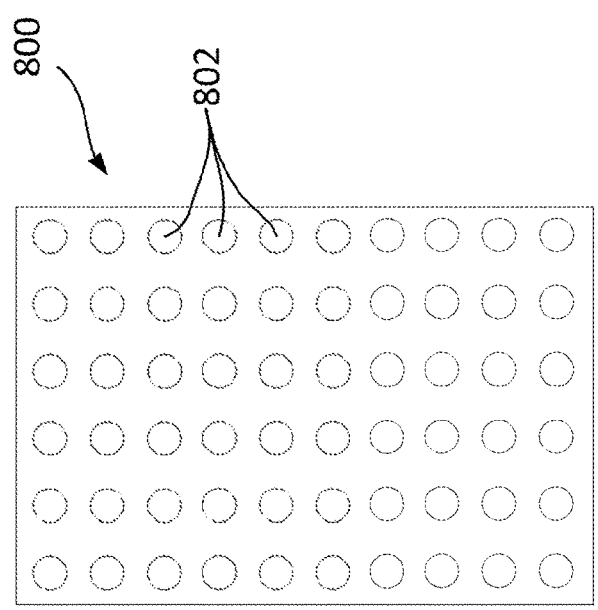
FIG. 15 is a plan view of a rectangular array of hair transplant devices in accordance with the present disclosure.

Referring now to FIGS. 15-17, several different possible matrices are illustrated that are capable of being operated by the hair transplant system 700. As illustrated, the hair transplant system 700 is capable of operating matrices of varying shapes and configurations. In some instances, the hair transplant system 700 can operate a matrix 800 having a rectangular shape with evenly-spaced hair transplant devices 802, as shown in FIG. 15. In some other instances, the hair transplant system 700 can operate a matrix 900 having a circular shape and evenly-spaced hair transplant devices 902, as shown in FIG. 16. In yet some other instances, the hair transplant system 700 can operate a matrix 1000 having a circular shape and unevenly-spaced hair transplant devices 1002, as shown in FIG. 17. As such, the hair transplant system 700 can operate matrices of any suitable shape or size, with evenly or unevenly spaced hair transplant devices, as desired by the doctor or other hair transplant procedure personnel.

For example, in some instances, matrices can be designed to implant entire pre-designed hair line implants simultaneously. For example, if it is desired to create a natural-looking hair pattern, such as, for example, a widow's peak, a cowlick, or any other desired hair pattern, a matrix can be designed using a plurality of hair transplant devices in a desired shape, distribution, and angulation to create the desired hair pattern.

Further, each of the coring elements, splitting elements, and pins of the hair transplant devices within each of the arrays may be linked, such that the hair transplant system 700 can effectuate all of the coring elements, splitting elements, or pins simultaneously.

Alternatively, the hair transplant system 700 can be configured to rapidly effectuate the hair transplant device 709 to create any desired hair line and/or hair pattern in a hair-by-hair fashion.

Figure 19:
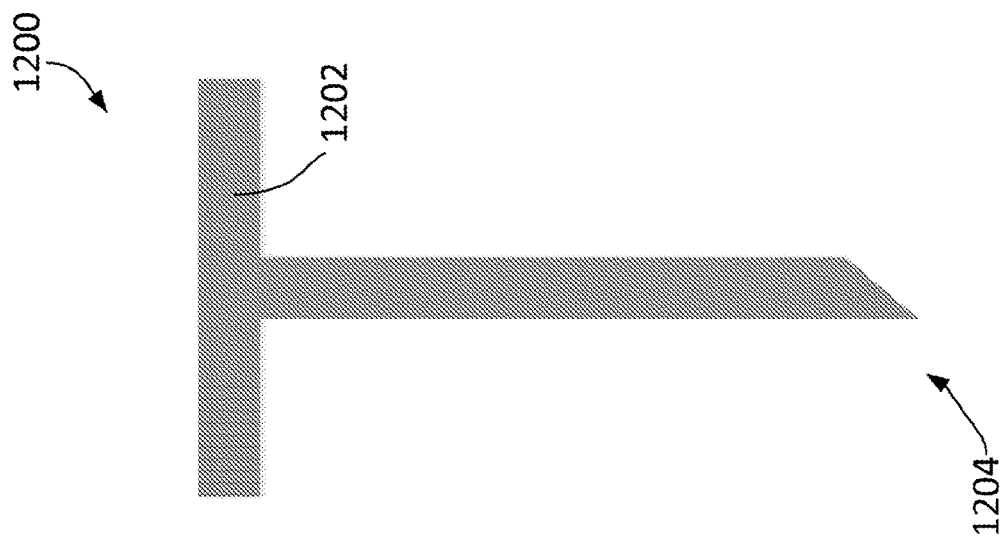
FIG. 19 is a cross-sectional view of a splitting device in accordance with the present disclosure.
Figure 18:
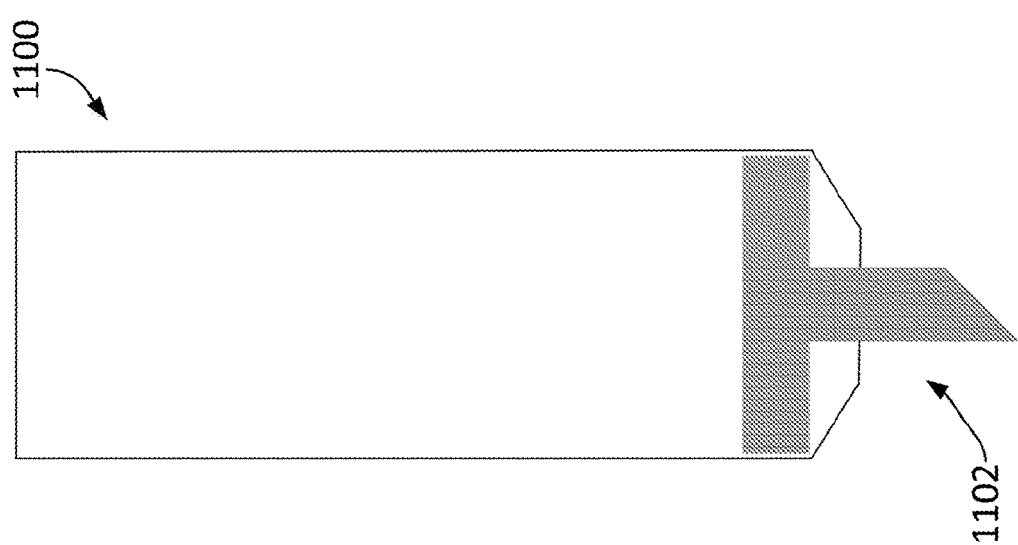
FIG. 18 is a cross-sectional view of a splitting device in accordance with the present disclosure.

Referring now to FIGS. 18 and 19, various splitting devices and elements can be used in conjunction with or in lieu of the various splitting devices and elements described above to create openings within the recipient site of a recipient. For example, in some instances, a splitting device 1100 can be provided that includes a splitting element 1102 that comprises a blade. The blade in these instances does not include a lumen and therefore does not have to be disposed coaxially with the coring needle. Similarly, in some instances, a splitting device 1200 can be provided that includes a handle 1202 and a splitting element 1204 that comprises a sharp stylet. Again, in these instances, the splitting element 1204 does not include a lumen and therefore does not have to be disposed coaxially with the coring needle.

Figure 20C:
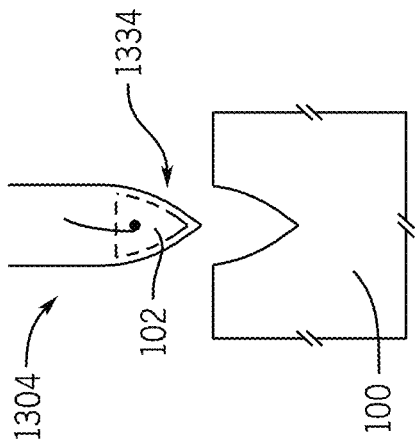
FIG. 20C is a cross-sectional view of a coring needle in accordance with the present disclosure, shown containing a skin core within a donor site, the coring needle being in an opened orientation.
Figure 20D:
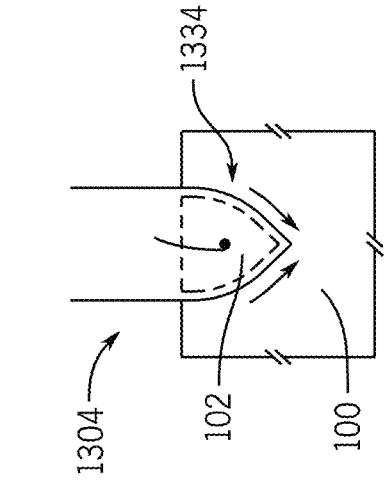
FIG. 20D is a cross-sectional view of the coring needle of FIG. 20C, shown containing the skin core within the donor site, the coring needle being in a closed orientation.
Figure 20E:
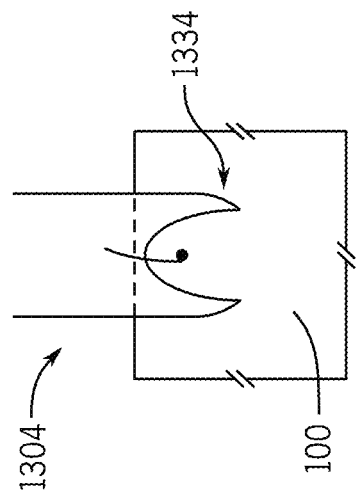
FIG. 20E is a cross-sectional view of the coring needle of FIG. 20D, shown containing the skin core removed from the donor site.
Figure 20F:
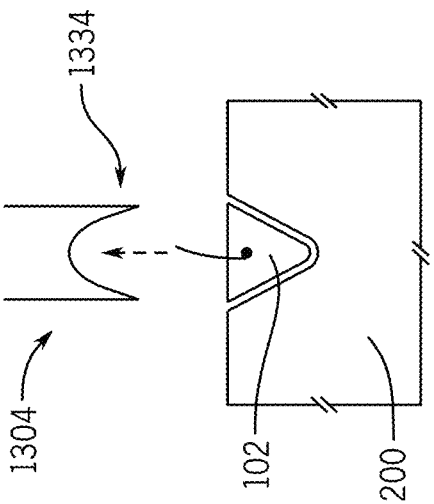
FIG. 20F is a cross-sectional view of the coring needle of FIG. 20E, shown containing the skin core and inserted into a recipient site, the coring needle being in the closed orientation.
Figure 20G:
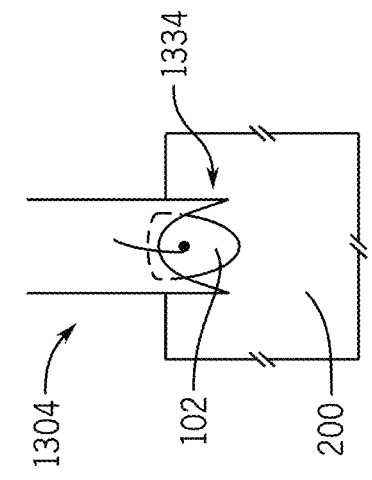
FIG. 20G is a cross-sectional view of the coring needle of FIG. 20F, shown containing the skin core within the recipient site, the coring needle being in the opened orientation.
Figure 20H:
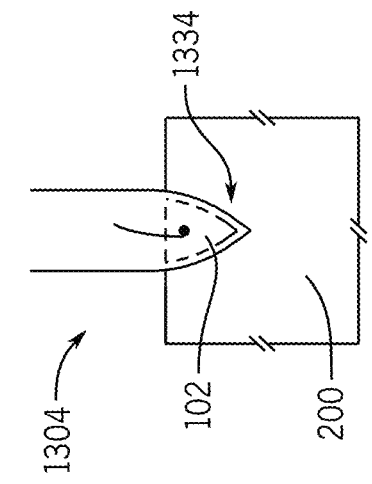
FIG. 20H is a cross-sectional view of the coring needle of FIG. 20G, shown removed from the recipient site, with the skin core remaining within the recipient site.

Referring now to FIGS. 20A and 20B, a hair transplant device 1300 substantially similar to the hair transplant device 10 is illustrated. The hair transplant device 1300 includes a housing 1302 containing a coring element 1304, a splitting element 1306, and a user interface 1308.

The housing 1302, the coring element 1304, and the user interface 1308 each function identically to the housing 12, the coring element 14 and the user interface 18. The splitting element 1306, however, has a slightly different structure and function than the splitting element 16.

Specifically, the splitting element 1306 includes a distal cutting end 1310 having a pair of movable walls 1312 that are movable between a closed orientation, where the pair of movable walls 1312 form a distal cutting point 1314, as shown in FIG. 20A, and an opened orientation, where the pair of movable walls 1312 are bent away from each other, as shown in FIG. 20B. The distal cutting end 1310 may be naturally biased toward the closed orientation. In some instances, the pair of movable walls 1312 may comprise two sharp-tipped, pointed half round metal pieces that are attached to each other at one end. The splitting element 1306 may be disposed around the shaft of the coring element 1304 and arranged so that cutting tips of the coring element 1304 are offset from cutting tips of the splitting element 1306.

During the extraction procedure, the coring element 1304 can be pushed through the distal cutting end 1310, thereby forcing the pair of movable walls 1312 apart, into the opened orientation. With the coring element 1304 pushed through the distal cutting end 1310, the coring element 1304 can be used to extract the skin core 102 from the donor site 100. In some instances, with the coring element 1304 inserted into the donor site 100, the splitting element 1306 may be advanced, or the coring element 1304 may be retracted, such that the distal cutting end 1310 can move toward the closed orientation. This closure of the distal cutting end 1310 may aid in the extraction of the skin core 102 by cutting or grabbing the tissue of the skin core 102.

While creating the opening in the recipient site 200, the distal cutting end 1310 is in the closed orientation. With the distal cutting end 1310 in the closed orientation, the distal cutting point 1314 splits the tissue of the recipient site 200 to create the opening. With the distal cutting end 1310 disposed within the tissue of the recipient site 200, the coring element 1304, which, as illustrated, can contain a skin core 102, can be pushed through the distal cutting end 1310, thereby forcing the pair of movable walls 1312 apart, into the opened orientation. With the coring element 1304 pushed through the distal cutting end 1310, the skin core 102 can be implanted within the recipient site 200 at a desired depth within the recipient site 200, thereby allowing for precise positioning of the skin core 102 within the scalp tissue of the recipient site 200. Once the skin core 102 has been implanted within the recipient site 200, the hair transplant device 1300 can once again be used to extract another skin core 102 from the donor site 100.

In some instances, the pair of movable walls 1312 are made of a material that changes shape in response to external cues (e.g. temperature). As such, the pair of movable walls 1312 is configured to move between the closed and opened orientations based on a heat memory of the material of the splitting element 1306. For example, in some instances, when the splitting element 1306 is at room temperature, it can be configured to remain in the closed orientation. Then, when the splitting element 1306 is inserted into the tissue, the temperature increase associated with the tissue can result in the splitting element 1306 moving into the opened orientation, thereby providing a channel within the recipient site 200 for the skin core 102 to be implanted into. In some instances, the splitting element 1306 can be configured to remain in the opened orientation at room temperature. Then, when the splitting element 1306 is inserted into the tissue, the temperature increase associated with the tissue can result in the splitting element 1306 moving into the closed orientation, thereby aiding in the removal of the skin core 102 from the donor site 100.

Referring to FIG. 20C-20H, in some instances, the splitting element 1306 is excluded, and the coring element 1304 includes a distal cutting end 1334, similar to the distal cutting end 1310, that is similarly made of a material that changes shape in response to external cues (e.g. temperature). Accordingly, the distal cutting end 1334 can be open before insertion into the donor site 100. Then, once the distal cutting end 1334 is inserted into the donor site 100, the distal cutting end 1334 is configured to move into a closed orientation due to the heat memory of the material. For example, the distal cutting end 1334 may comprise a bimetallic material or a combination of materials having differing thermal expansion coefficients to provide the natural actuation between the opened and closed orientations. In some instances, the bimetallic material may comprise steel and copper. In other instances, any other suitable materials may be used that provide the necessary thermal expansion properties.

When the distal cutting end 1334 closes, the skin core is severed and trapped within the coring element 1304. With the distal cutting end 1334 in the closed orientation, the coring element 1304 can be used to insert the skin core 102 into the recipient site 200. With the coring element 1304 inserted into the recipient site 200, the distal cutting end 1334 can be opened by, for example, applying heat or cooling to the coring element 1304, so that the coring element 1304 can be withdrawn, leaving behind the skin core 102.

Figure 21B:
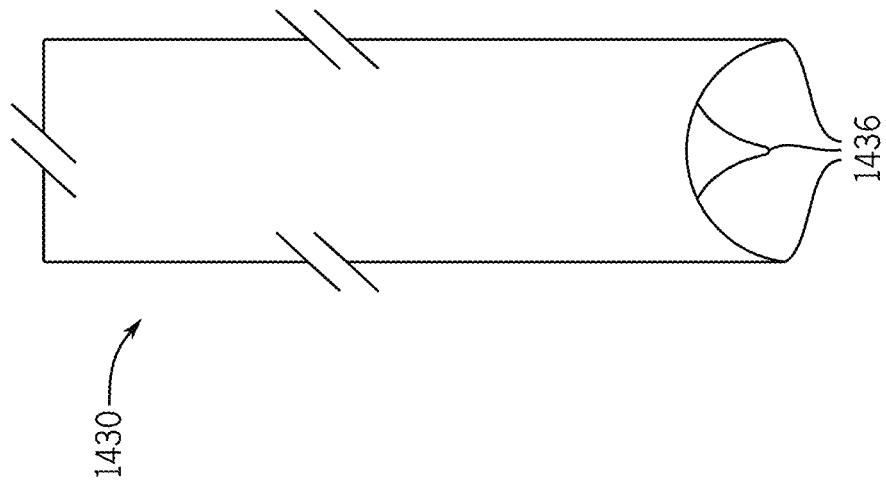
FIG. 21B is a perspective view of another coring needle in accordance with the present disclosure.
Figure 21A:
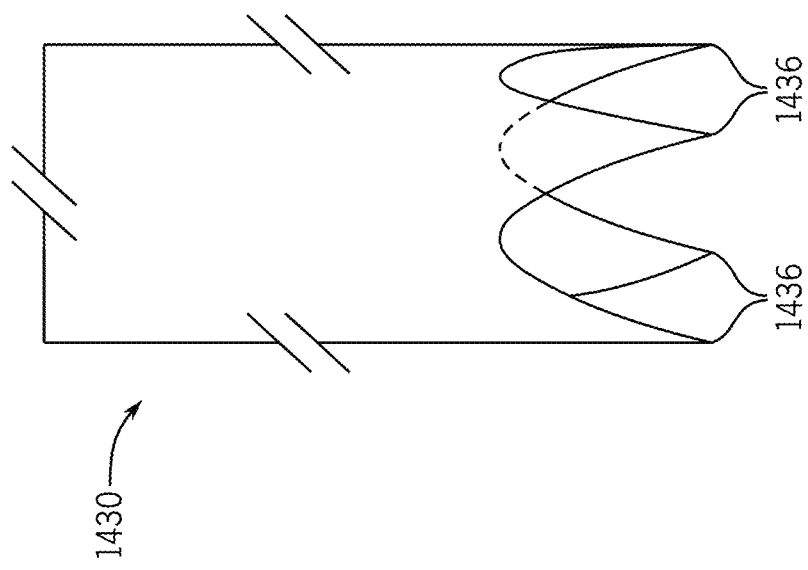
FIG. 21A is a perspective view of a coring needle in accordance with the present disclosure.

Referring to FIGS. 21A and 21B, a coring needle 1430 is illustrated. The coring needle 1430 is configured for use with any of the devices, systems, and methods described herein. As shown, the coring needle 1430 includes a plurality of cutting edges 1436. In the illustrated non-limiting examples, the coring needle 1430 may include four cutting edges 1436 (as shown in FIG. 21A) or three cutting edges 1436 (as shown in FIG. 21B). In other examples the coring needle 1430 may include more than four cutting edges 1436 or less than three cutting edges 1436, as desired for a particular procedure.

With fewer cutting edges 1436, the epidermal area may end up being cut in a semi-ovoid shape during extraction. This may result in a larger skin core being extracted from the donor site 100, as compared to a perfectly round skin core. In some instances, it may be beneficial to minimize the skin core size during extraction. In these cases, increasing the number of cutting edges 1436 may allow for a more uniform diameter skin core to be extracted. The additional cutting edges 1436 increase the force needed to push the coring needle 1430 through the scalp tissue.

Figure 21C:
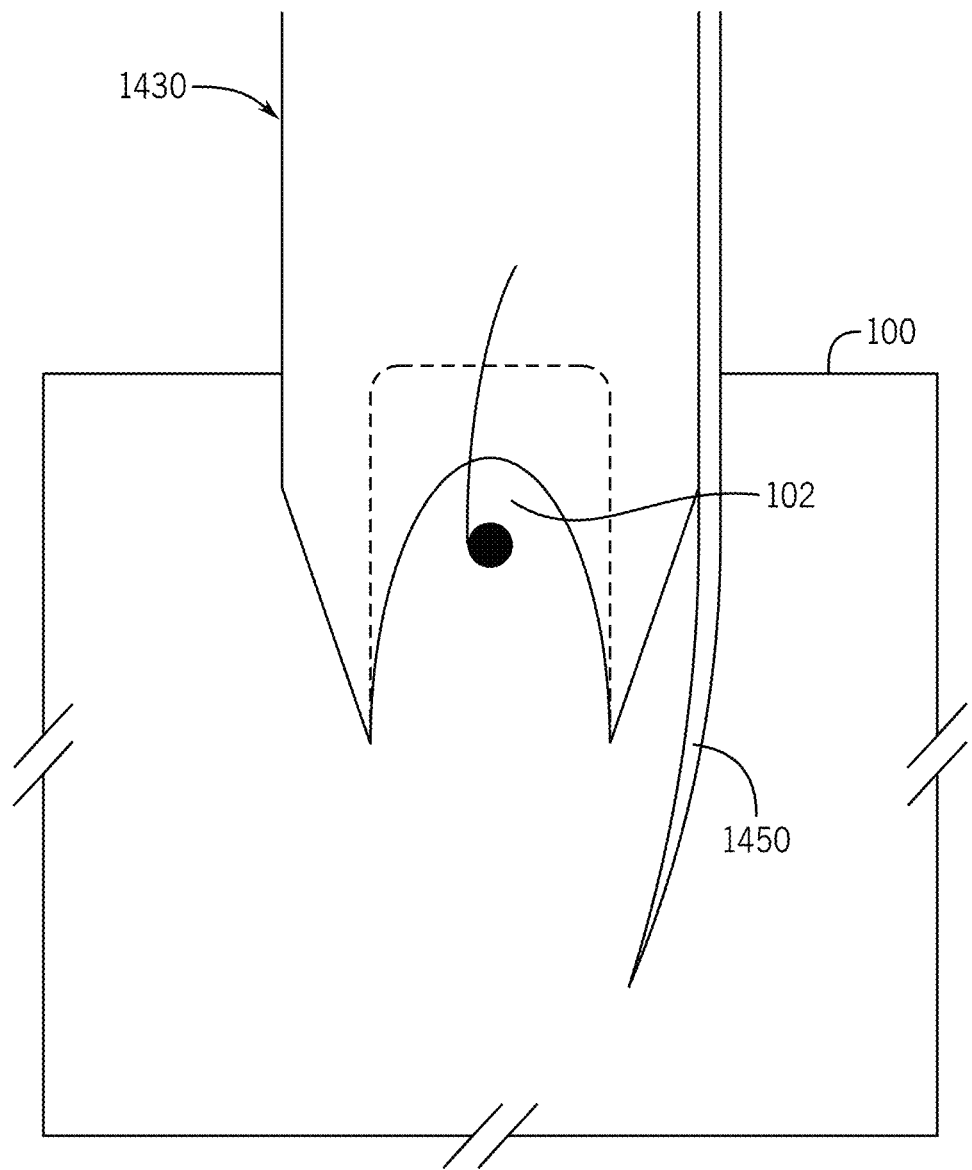
FIG. 21C is a cross-sectional view of a coring needle in accordance with the present disclosure, the coring needle including a flat wire to aid in extraction of the skin core.

Referring now to FIG. 21C, in some other instances, extraction of the skin core 102 from the donor site 100 may be further aided using a flat wire 1450. The flat wire 1450 can be advanced to aid in cutting, tearing, and/or separating the skin core 102 from the donor site 100. In the illustrated non-limiting example, there is a single flat wire 1450 arranged on the outside of the coring needle 1430. In other non-limiting examples, there can be two wires opposite each other that are either on the inside or outside the of the coring needle 1430. In these instances, when the two wires are advanced along the coring needle 1430, they can come toward each other and to cut or grab the skin core 102, thereby aiding in removal.

Figure 22A:
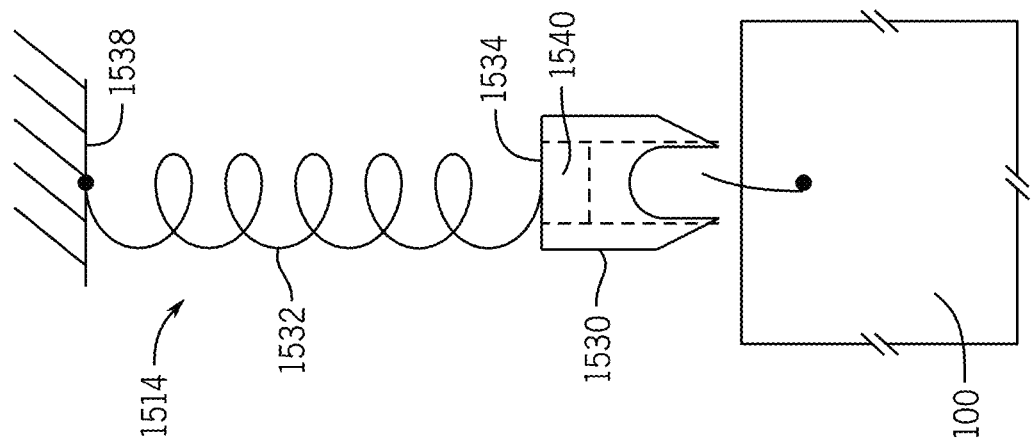
FIG. 22A is a cross-sectional view of a coring element in accordance with the present disclosure, shown with a coring needle in a spring-loaded position.
Figure 22B:
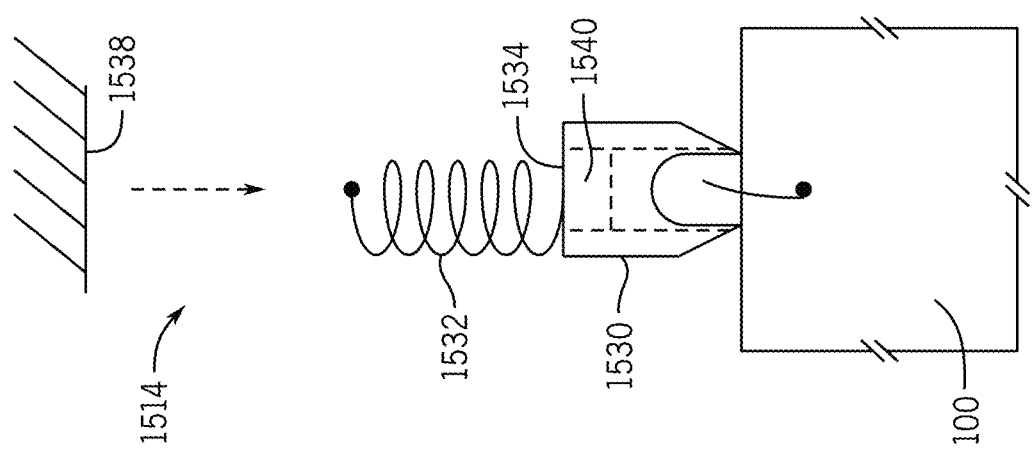
FIG. 22B is a cross-sectional view of the coring element of FIG. 22A, shown with the coring needle moving toward the donor site.
Figure 22C:
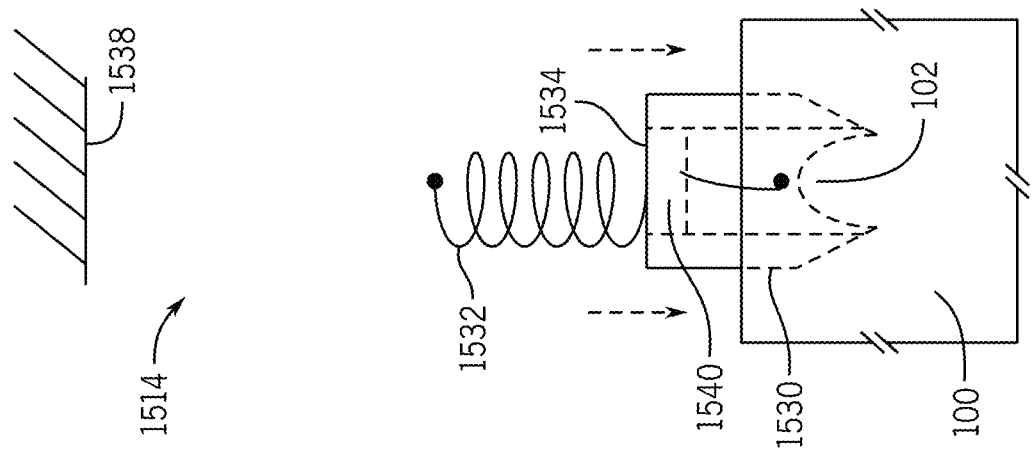
FIG. 22C is a cross-sectional view of the coring element of FIG. 22B, shown with the coring needle inserted into the donor site.

Referring now to FIGS. 22A-22C, another coring element 1514 is illustrated. The coring element 1514, or in some devices several coring elements similar to the coring element 1514, may be employed within a handheld or automated hair transplant device, such as any of the devices, systems, and methods described herein. The coring element 1514 includes a coring needle 1530 and a spring 1532.

During the extraction procedure, the coring needle 1530 can be actuated in a spring-loaded manner, using the spring 1532. For example, in the illustrated non-limiting example, the spring 1532 is coupled between a proximal surface 1534 of the coring needle 1530 and a surface 1538 within the corresponding hair transplant device, such as, for example, the user interface. The spring 1532 is initially stretched past its natural resting length, thereby spring-loading the coring needle 1530, as shown in FIG. 22A. With the coring needle 1530 positioned and aligned over the donor site 100, the spring 1532 is quickly released from the surface 1538, causing a propagational force to drive the coring needle 1530, or, in some instances, a group of needles, into the donor site 100.

In some instances, a pin 1540, or multiple pins, may be included within the coring element 1514, or the several coring elements, and the distal end of the spring 1532 can be coupled to the pin 1540, such that pulling back on the spring 1532 creates a suction within the coring element 1514, to aid in pulling the skin core(s) 102 out of the donor site 100.

During the implantation procedure, the coring element(s) 1514 and corresponding splitting elements (not shown), similar to the splitting elements described above, may be positioned on the recipient site 200. The spring 1532 may be restretched or loaded, and subsequently similarly used to drive both a splitting needle of the splitting element and the coring needle 1530, disposed within the splitting needle, into the tissue. In some instances, the pin 1540 can be arranged on the inside of the spring 1532, and can be actuated to implant the skin core 102 into the recipient site 200. In some other instances, the spring 1532 may be arranged on the exterior Prior to the implantation procedure, key holes may be formed in the recipient site 200 by using a hollow spike or a series of hollow spikes. The spikes may be positioned on the recipient site 200 and the skin cores 102 within the coring needles may be deployed into the recipient site 200 through the spikes using the pins. In some instances, the spikes may be made of two halves, attached by a spring-loaded mechanism (e.g., similar to the mechanism in a clothes pin), such that the spikes may be opened and removed after the skin cores 102 have been deployed into the recipient site 200.

Figure 23A:
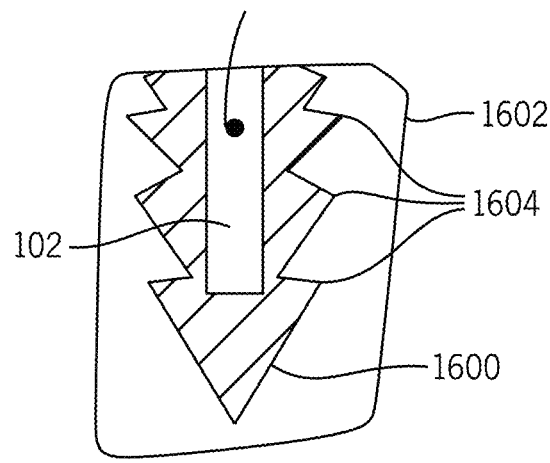
FIG. 23A is a cross-sectional view of a mold containing a molded spike and a skin core for implantation, in accordance with the present disclosure.
Figure 23B:
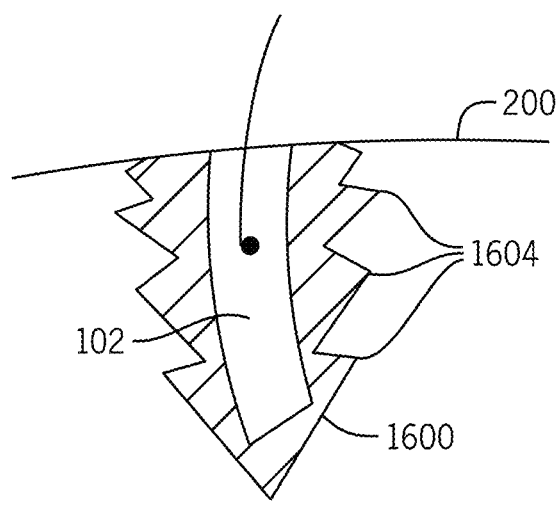
FIG. 23B is a cross-sectional view of the molded spike and the skin core of FIG. 23A implanted within a recipient site.

As shown in FIGS. 23A and 23B, in some instances, the skin core 102 can be embedded in a molded spike 1600 created using a mold 1602. The molded spike 1600 has a spiked shape to ease insertion into recipient site 200. The molded spikes 1600 can have ridges or flanges 1604 to help anchor them into the recipient site 200. The molded spikes 1600 can be made of a biomaterial/polymer material having a freezing temperature lower than skin temperature, but not so low as to damage the skin (e.g., room temperature). Accordingly, the molded spikes 1600 can be formed around the skin core 102 and subsequently forced into the recipient site 200. In some instances, the molded spikes 1600 can be forced into the recipient site using ballistic or pneumatic mechanisms. These mechanisms may function similar to a staple or nail gun.

In some instances, the devices, systems, and methods disclosed herein may be automated, for example, using a robotic system. For example, a robotic arm made for medical uses may be utilized to increase precision of the processes disclosed herein. For example, a series of coring needles may be loaded onto the end of the robotic arm. The coring needles may be configured so that each coring needle may be positioned angularly or moved closer or further apart from each other. The robotic arm may be controlled by computer vision (i.e., a camera may be utilized to align the robotic arm along a hair shaft or a plurality of hair shalves).

In some non-limiting examples, the camera could be a standard Cmos camera or an OCT imaging device. The OCT imaging device may allow for more precise alignment of the robotic arm with reference to the hair shalves due to the capability of OCT imaging to see vertically into the tissue. Once the skin cores have been extracted, the robotic arm may position itself over the recipient site for implantation of the hairs. A computer image may similarly be obtained of the recipient site that may show a natural hair line for the patient and direct where the hairs should be implanted. The ability of the needles to move independently may allow for better shaping and following of a natural hair line. In some instances, the patient may be positioned in a support holder or laying down to limit movement during this process.

As such, the devices, systems, and methods described herein allow for a user to extract at least one hair follicle from a donor site, create at least one opening in a recipient site, and implant the at least one hair follicle in the at least one opening repetitively using a single device without the need for any physical manipulation of the at least one hair follicle. Accordingly, these devices, systems, and methods allow for more efficient, reliable, and predictable hair transplant procedures than compared to traditional devices, systems, and methods.

The present invention has been described in terms of one or more preferred embodiments, and it should be appreciated that many equivalents, alternatives, variations, and modifications, aside from those expressly stated, are possible and within the scope of the invention.

The invention claimed is:

1. A hair transplant device comprising:
    a coring needle forming a coring lumen configured to extract a hair follicle from a donor site;
    a splitting needle configured to create an opening in a recipient site;
    a housing at least partially surrounding one of the coring needle and the splitting needle; and
    a user interface including a pin, the user interface extending from the housing and movable relative to the coring needle to push the hair follicle from the coring lumen into the opening in the recipient site formed by the splitting needle;
    wherein the coring needle and the splitting needle are coaxially disposed within the housing, and are movable relative to the housing, such that the coring needle and the splitting needle are selectively and individually movable,
    wherein the user interface is movable between a retracted position and an inserted position, and a distal tip of the pin of the user interface is prevented from extending distally past the splitting needle and the coring needle,
    wherein the coring needle is moved distally relative to the housing to allow for extraction of the hair follicle.

2. The device of claim 1, wherein the coring needle includes at least two angled cutting surfaces at a distal end of the coring needle.

3. The device of claim 2, wherein the coring needle includes at least three distal cutting edges.

4. The device of claim 1, wherein the pin of the user interface forms a central lumen configured to deliver a suction force into the coring lumen of the coring needle to effectuate extracting the hair follicle from the donor site.

5. The device of claim 4, wherein the coring lumen includes a porous stop configured to prevent the hair follicle from being drawn past a predetermined position within the coring lumen.

6. The device of claim 1, wherein the pin of the user interface forms a central lumen in fluid communication with the coring lumen to deliver a gas or a liquid into the coring lumen of the coring needle while implanting the hair follicle into the recipient site.

7. The device of claim 1, wherein the user interface configured to move a predetermined amount relative to the housing to control a depth of delivery of the hair follicle within the opening in the recipient site.

8. The device of claim 1, wherein one of the coring needle and the splitting needle is arranged relative to the housing to engage the donor site or the recipient site at a predetermined angle that is non-normal,
wherein the non-normal angle is less than or equal to 60 degrees.

9. The device of claim 1, further comprising a matrix configured to engage and align a plurality of respective coring needles, splitting needles, housings, and user interfaces to perform multiple extractions and implantations of hair follicles simultaneously or sequentially.

10. The device of claim 1, wherein the coring needle includes a wire configured to aid in separation of the hair follicle from the donor site.

11. The device of claim 1, wherein at least one of the coring needle and the splitting needle are spring-loaded for selectively actuating the at least one of the coring needle and the splitting needle into at least one of the donor site and the recipient site.

12. The device of claim 1, wherein the splitting needle includes a distal cutting end having a pair of movable walls that are moveable between a closed orientation and an opened orientation, the pair of movable walls being biased toward the closed orientation, and the coring needle is configured to selectively force the pair of movable walls into the opened orientation.

13. A hair transplant system comprising:
a matrix arranging a plurality of hair transplant devices to perform multiple extractions and implantations of hair follicles in a coordinated manner, each of the plurality of hair transplant devices comprising:
a coring needle forming a coring lumen configured to extract a hair follicle from a donor site of a subject;
a splitting needle configured to create an opening in a recipient site of the subject;
a housing at least partially surrounding one of the coring needle and the splitting needle; and
a user interface including a pin, the user interface extending from the housing and movable relative to the coring lumen to implant the hair follicle within the recipient site by pushing the hair follicle from within the coring lumen into the opening in the recipient site,
wherein the coring needle and the splitting needle are coaxially disposed within the housing, and are movable relative to the housing, such that the coring needle and the splitting needle are selectively and individually movable,
wherein the user interface is movable between a retracted position and an inserted position, and a distal tip of the pin of the user interface is prevented from extending distally past the splitting needle and the coring needle, and
wherein the coring needle is moved distally relative to the housing to allow for extraction of the hair follicle.

14. The hair transplant system of claim 13, wherein the plurality of hair transplant devices perform extraction of a plurality of hair follicles from the donor site simultaneously, creation of a plurality of openings in the recipient site simultaneously, and implantation of the plurality of hair follicles within the recipient site simultaneously.

15. The hair transplant system of claim 14, wherein the matrix forms a two dimensional array of hair transplant devices including tens, hundreds, or thousands of hair transplant devices configured to perform the extraction of tens, hundreds, or thousands of hair follicles from the donor site simultaneously, the creation of tens, hundreds, or thousands of openings in the recipient site simultaneously, and the implantation of the tens, hundreds, or thousands of hair follicles within the recipient site simultaneously.

16. The hair transplant system of claim 13, wherein a distribution and separation between the plurality of hair transplant devices in the matrix is adjustable.

17. The hair transplant system of claim 16, further comprising a controller configured to adjust the distribution and separation between the plurality of hair transplant devices.

18. The hair transplant system of claim 13, further comprising a controller configured to adjust an angle of the coring needles relative to the donor site or the recipient site to allow for the hair follicles to be extracted or implanted in desired orientations.

19. The hair transplant system of claim 13, wherein, for each of the hair transplant devices, the pin of the user interface forms a central lumen to deliver a suction force into the coring lumen of the coring needle to effectuate extracting the hair follicle from the donor site.

20. The hair transplant system of claim 13, wherein, for each of the hair transplant devices, the pin of the user interface forms a central lumen in fluid communication with the coring lumen to deliver a gas or a liquid into the coring lumen of the coring needle while implanting the hair follicle into the recipient site.

21. The hair transplant system of claim 13, wherein, for each of the hair transplant devices, the pin of the user interface forms a central lumen in fluid communication with the coring lumen to deliver a gas or a liquid into the coring lumen of the coring needle while extracting the hair follicle from the donor site, thereby pushing long hairs away from the coring needle and allowing for the long hairs to remain untrimmed while extracting the hair follicle from the donor site.

22. The hair transplant system of claim 13, wherein the matrix is configured to implant an entire pre-designed hair line implant simultaneously.

23. A method of performing a hair transplant procedure using an automated transplant device, the method comprising:
engaging a user interface to cause a coring needle having a coring lumen to engage a donor site of a donor to arrange a hair follicle within the coring lumen of the coring needle;
further engaging the user interface to cause a splitting needle to deploy from a housing and create an opening within a recipient site of a subject; and further engaging the user interface to displace the hair follicle from the coring lumen to implant the hair follicle within the opening in the recipient site;

wherein the coring needle and the splitting needle are coaxially disposed within the housing, and are movable relative to the housing, such that the coring needle and the splitting needle are selectively and individually deployable, and wherein the user interface includes a pin, the user interface extends from the housing and is movable between a retracted position and an inserted position, and a distal tip of the pin of the user interface is prevented from extending distally past the splitting needle and the coring needle; and wherein the coring needle is moved distally relative to the housing to allow for extraction of the hair follicle.

24. The method of claim 23, wherein the user interface is configured to control a plurality of coring needles and splitting needles to effectuate multiple individual extractions of hair follicles from respective donor sites, creation of respective openings within respective recipient sites, and displacement of respective hair follicles into the respective openings at the recipient sites.

25. The method of claim 23, wherein the pin of the user interface is configured to implant the hair follicle within the recipient site by pushing the hair follicle from within the coring lumen into the opening in the recipient site.

* * * * *